(12) United States Patent
Liu

(10) Patent No.: US 9,937,214 B2
(45) Date of Patent: Apr. 10, 2018

(54) LACTOBACILLUS CRISPATUS AND APPLICATION THEREOF

(71) Applicant: Suzhou Osel Bio-Pharm Co., Ltd., Suzhou (CN)

(72) Inventor: Yang Liu, Suzhou (CN)

(73) Assignee: Suzhou Osel Bio-Pharm Co., Ltd., Shijiazhuang, Hebei (CN)

( * ) Notice: Subject to any disclaimer, the term of this patent is extended or adjusted under 35 U.S.C. 154(b) by 0 days.

(21) Appl. No.: 15/034,503

(22) PCT Filed: Oct. 30, 2014

(86) PCT No.: PCT/CN2014/089882
§ 371 (c)(1),
(2) Date: May 4, 2016

(87) PCT Pub. No.: WO2015/067141
PCT Pub. Date: May 14, 2015

(65) Prior Publication Data
US 2017/0020934 A1     Jan. 26, 2017

(30) Foreign Application Priority Data

| Nov. 8, 2013 | (CN) | 2013 1 0551630 |
| Nov. 8, 2013 | (CN) | 2013 1 0551661 |
| Dec. 26, 2013 | (CN) | 2013 1 0731833 |

(51) Int. Cl.
| A61K 35/747 | (2015.01) |
| A61K 8/99 | (2017.01) |
| C12R 1/225 | (2006.01) |
| A61Q 19/00 | (2006.01) |
| A61K 35/74 | (2015.01) |
| A61K 35/00 | (2006.01) |

(52) U.S. Cl.
CPC .............. *A61K 35/747* (2013.01); *A61K 8/99* (2013.01); *A61Q 19/00* (2013.01); *C12R 1/225* (2013.01); *A61K 35/74* (2013.01); *A61K 2035/11* (2013.01); *A61K 2035/115* (2013.01)

(58) Field of Classification Search
None
See application file for complete search history.

(56) References Cited

U.S. PATENT DOCUMENTS

| 8,329,447 B2 | 12/2012 | Liu et al. |
| 2002/0090365 A1 | 7/2002 | Chrisope |

OTHER PUBLICATIONS

Hemmerling et al., Sexually Transmitted Disease, 2010, vol. 37, No. 12 p. 745-750.*
Ngugi et al., Effects of BV-Associated Bacteria and Sexual Intercourse on Vaginal Colonization with the Probiotic *Lactobacillus crispatus* CTV-05, Sex. Transm. Dis., Nov. 2011, pp. 1020-1027, vol. 38(11).

* cited by examiner

*Primary Examiner* — Kade Ariani
(74) *Attorney, Agent, or Firm* — Knobbe Martens Olson & Bear LLP

(57) ABSTRACT

The present invention discloses *Lactobacillus crispatus* 262-1 and an inoculum comprising such strain and application thereof. The *Lactobacillus crispatus* 262-1 is a new strain of *Lactobacillus* genus and is preserved in the China General Microbiological Culture Collection Center with a preservation number of CGMCC No. 6469. The *Lactobacillus crispatus* 262-1 particularly is the dominant bacteria in the vagina, has good acid and $H_2O_2$ production capability, good adhesion to the vaginal epithelial cells and significant resistance to bacterial vaginosis and various vaginal infections, and is characterized by safety, non-toxicity, good stability and long term preservation. The present invention also relates to the use of the *Lactobacillus crispatus* 262-1 in the preparation of pharmaceuticals for preventing and/or treating gynecological diseases and its application in feminine care products such as medical instruments, disinfect products or cosmetics.

15 Claims, 12 Drawing Sheets

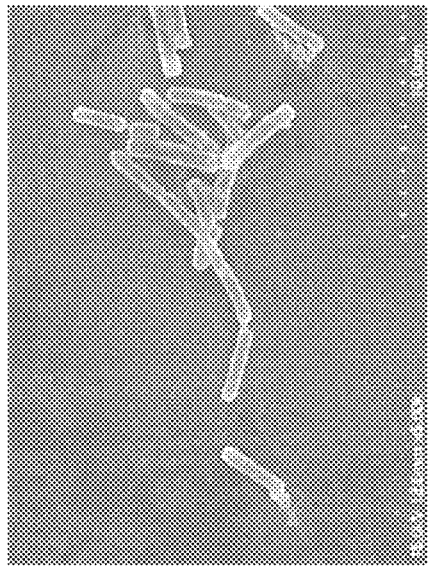
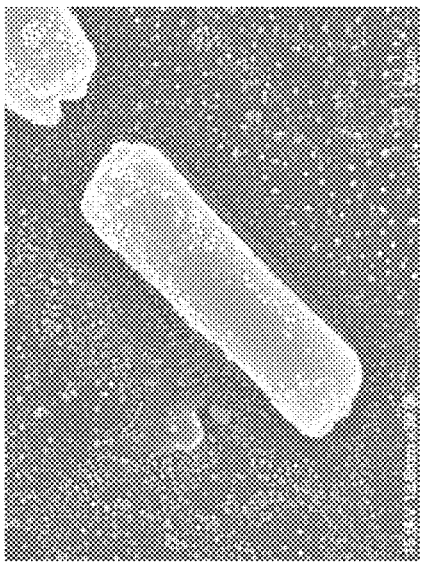
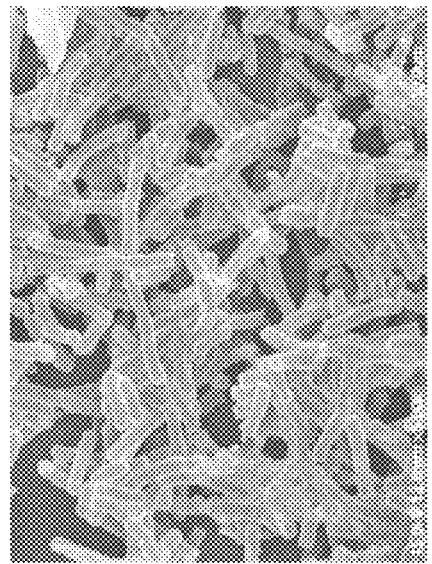
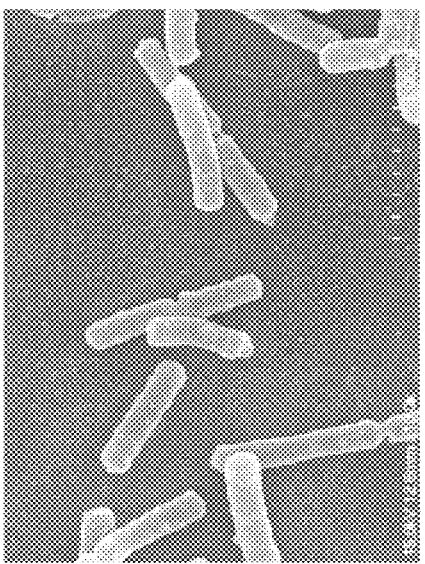
FIG. 3A
FIG. 3B
FIG. 3C
FIG. 3D

LACTOBACILLUS CRISPATUS AND APPLICATION THEREOF

RELATED APPLICATIONS

This application is the U.S. National Phase under 35 U.S.C. § 371 of International Application No. PCT/CN2014/089882 entitled "*LACTOBACILLUS CRISPATUS* AND APPLICATION THEREOF," filed Oct. 30, 2014, designating the U.S.; which claims priority to Chinese Patent Application No. 201310731833.0, filed Dec. 26, 2013, Chinese Patent Application No. 201310551661.9, filed Nov. 8, 2013, and Chinese Patent Application No. 201310551630.3, filed Nov. 8, 2013. The contents of these related applications are herein expressly incorporated by reference in their entireties.

BACKGROUND

Field of the Invention

The present invention relates to a new bacterial strain of *Lactobacillus* and application thereof, specifically relates to a *Lactobacillus crispatus*, which has an effect of evidently inhibiting *Candida albicans* and pathogens while regulating vaginal microenvironment and inhibiting *Gardnerella vaginalis* (BV pathogenic bacteria), and has enormous advantage and potential in applying to the preparation of pharmaceuticals for treating bacterial vaginosis combined fungal infection which is most common in clinic and to the preparation of daily feminine health products.

Description of the Related Art

Multiple microorganisms exist in a healthy woman's vagina, and form a vaginal micro-ecosystem of mutual restriction, mutual coordination and dynamic equilibrium with the host and the environment. The vaginal flora in the healthy woman is primarily constituted by *Lactobacillus*, comprising *Lactobacillus crispatus, Lactobacillus Jensenii* and *Lactobacillus gasseri*, etc. The *Lactobacillus* can protect the vagina under normal circumstances, while a disorder of *Lactobacillus*-predominant vaginal micro-ecosystem can cause vaginitis.

Occurrence of bacterial vaginosis (BV) is caused by massive propagation of other conditional pathogenic microorganisms such as *Gardnerella vaginalis*, various anaerobic bacteria, *campylobacter* and the like due to vaginal dysbacteriosis and reduction of *lactobacillus* of the host per se. The BV is actually a kind of *Gardnerella vaginalis*-based mixed infection. Although the application of antibiotic treatment may respite the symptoms of the BV, it even further reduces the *lactobacillus* which has been reduced, exacerbating vaginal micro-ecology dysbiosis and therefore causing repeated recurrence of the BV. How to control the recurrence and thoroughly cure the bacterial vaginosis are problematic issues that are necessarily to be solved by gynecologists.

Similarly, since the feminine vagina is easily susceptible to infections, in daily life, many women use gynecological disinfection products, care products and beauty care products to prevent diseases, keep hygiene or keep fit; however, various problems still often occur. Under normal circumstances, a large quantity of bacilli beneficial for human exist in the vagina, decompose glycogen in vaginal epidermal cell into lactic acid to maintain acidity in the vagina, thereby forming a natural defense that prevents pathogenic bacteria from propagation in the vagina. Use of disinfector to rinse or soak in a hip bath may damage the defense function of the vagina, thus various pathogenic bacteria propagate in the vagina in a massive scale, causing various gynecological diseases. The aforementioned issues exist for cosmetics for pudendum as well. If not cared properly, bacteria could easily breed, causing itching, inflammation or even gynecological inflammation.

On the other hand, medical instruments, as the products of modern science technology, have been widely used in the processes of prevention, diagnosis and treatment of diseases, and health care and rehabilitation, and become an important diagnosis and treatment means in modern medical field. However, the medical instruments, like the pharmaceuticals, also have certain risks due to the impacts of factors such as design, material and clinical application. In the inspection, diagnosis and treatment process of gynecological diseases, infection may be caused if the materials used in the inspection instrument are irrational, the instrument is unclean or the subject is oversensitive. Therefore, it is particularly important to improve the material, components and contact components with a human body of the gynecological medical instrument so as to enhance the biocompatibility of the instrument, reduce infection probability and ensure inspection safety.

Various *lactobacillus* existing in the vagina of a healthy woman have individual differences, and each strain of the *lactobacillus* has significantly difference in resistance to pathogenic bacteria. In the selection of *lactobacillus* probiotics, it needs to comprehensively consider the types, acid-producing ability, $H_2O_2$-producing ability, and adhesive ability to vaginal epithelial cells of the *lactobacillus*, wherein successful colonization of the *lactobacillus* in the vagina is the basis of the continuous actions of the *lactobacillus* and inoculants taking the *lactobacillus* as active ingredients, and is also the key factor for the curative effect of the *lactobacillus*. Studies have shown that: the $H_2O_2$-producing *lactobacillus* are the dominant bacteria in the vagina of a healthy woman, and are the key factors for protecting the vagina from the pathogenic infection, and furthermore, acids and some antimicrobial agents produced by *lactobacillus* metabolism can also effectively inhibit the growth of other bacteria. Current products on the market do not contain dominant flora for the vaginas of women in China, have poor colonization ability, are incapable of maintaining stable viable bacteria content, and thus cannot meet the requirements of the gynecological clinic.

In view of the above, it will bring good news to Chinese women to separate and screen the flora that is applicable to the vaginal health of the Chinese women, and to the study and development of corresponding pharmaceuticals, health care products, cosmetics and medical instruments.

SUMMARY

The technical problem to be solved by the present invention is to provide a *Lactobacillus crispatus* that is screened from healthy human body and has active and stable biological characteristics and strong bacteriostatic ability and application thereof.

For solving the aforementioned technical problem, the technical solution proposed in the present invention is as follows:

A isolated *Lactobacillus crispatus* named as *Lactobacillus crispatus* 262-1, deposited in the China General Microbiological Culture Collection Center with a accession number of CGMCC No. 6469.

The aforementioned *Lactobacillus crispatus* 262-1 was screened from the vaginal secretions of a Chinese healthy woman of childbearing age, and is preserved in the China General Microbiological Culture Collection Center (CGMCC for short) on 22 Aug. 2012; the address of the preservation authority is the Institute of Microbiology, Chinese Academy of Sciences, No. 3 of Courtyard No. 1, West Beichen Road, Chaoyang District, Beijing City, the preservation registration number is CGMCC No. 6469, and the strain is classified and named as *Lactobacillus crispatus*.

A separated DNA molecule, wherein the DNA molecule is extracted from the aforementioned separated *Lactobacillus crispatus* 262-1 with a preservation number of CGMCC No. 6469, the base sequence of the DNA molecule is subjected to sequence-similarity comparative analysis by means of a BLAST program, and the value of the highest homology to the base sequence of the *Lactobacillus crispatus* in the GenBank database is greater than 98%.

Application of said *Lactobacillus crispatus* 262-1 in the preparation of pharmaceuticals for inhibiting vaginal pathogenic bacteria.

Application of said *Lactobacillus crispatus* 262-1 in the preparation of pharmaceuticals for preventing and/or treating in vaginal diseases.

Application of said *Lactobacillus crispatus* 262-1 in the preparation of pharmaceuticals for regulating vaginal flora balance.

Application of said *Lactobacillus crispatus* 262-1 in the preparation of pharmaceuticals with the function of adhesion to vaginal epithelial cells.

Application of said *Lactobacillus crispatus* 262-1 in gynecological medical instruments.

Application of said *Lactobacillus crispatus* 262-1 in gynecological disinfection products.

Application of said *Lactobacillus crispatus* 262-1 in cosmetics for female vagina.

The strain of the *Lactobacillus crispatus* 262-1 of the present invention is screened from the vaginal secretions of a Chinese healthy woman of childbearing age. A large number of experiments show that the *Lactobacillus crispatus* 262-1 has outstanding capabilities of production of acids and $H_2O_2$ as well as adhesion to vaginal epithelial cells, and has functions imparted by its features in the abovementioned pharmaceuticals for inhibiting vaginal pathogenic bacteria, pharmaceuticals for preventing and/or treating vaginal diseases, pharmaceuticals for regulating vaginal flora balance, pharmaceuticals with the function of adhesion to vaginal epithelial cells, as well as gynecological healthcare products, such as gynecological medical instruments, gynecological disinfection products and cosmetics for female vagina.

An inoculant prepared by the abovementioned *Lactobacillus crispatus* 262-1, wherein the active ingredient of the inoculant is the *Lactobacillus crispatus* 262-1.

The inoculant is prepared by using the *Lactobacillus crispatus* 262-1 as the active ingredient, and is in a form of liquid, solid or gel, wherein the solid inoculant is in the form of capsule or tablet or powder. Accordingly, the inoculant also has various applications identical or similar to those of the *Lactobacillus crispatus* 262-1.

The beneficial effects produced by adopting the aforementioned technical scheme are as follows: (1) the strain of the *Lactobacillus crispatus* 262-1 of the present invention can be preserved for a long time, and can resist bacterial vaginosis and various vaginal infections, comprising *Candida albicans* vaginitis, gonorrhoea, viral vaginitis and urinary tract infection, etc.; (2) the strain of the present invention is directly collected from the healthy human body, has active and stable biological properties without domestication and rejuvenation process but directly entering the preparation process, the survival rate of living bacteria of the preparation lyophilized powder is high after being preserved for 6 months at 4° C.; and (3) the active ingredients of the strain and inoculant of the present invention have effects of inhibiting *Gardnerella vaginalis*, *Atopobium vaginae*, *Candida albicans*, *Staphylococcus aureus*, *Escherichia coli*, *Pseudomonas aeruginosa* and *salmonella*, compared with the commercially available control bacteria, said active ingredients are more advantageous in adhesion to the vaginal epithelial cells and primate vaginal colonisation capacity, and have enormous application potential in gynecological medical instruments, gynecological disinfect products and the cosmetics used for female pudendum.

BRIEF DESCRIPTION OF THE DRAWINGS

FIGS. 3A, 3B, 3C and 3D are the electronic microscopic photos of the *Lactobacillus crispatus* 262-1 of the present invention enlarged for different times;

FIG. 13 shows the amounts of detected *Lactobacillus crispatus* 262-1 in the tested animal after the colonization of the *Lactobacillus crispatus* 262-1 of the present invention, wherein the longitudinal axis shows the CFU value of the *Lactobacillus crispatus* 262-1 and the horizontal axis represents 5 sampling time points of various animals; and day 1 represents the first day after colonization, and so on.

PRESERVATION INFORMATION

Figure 1A:
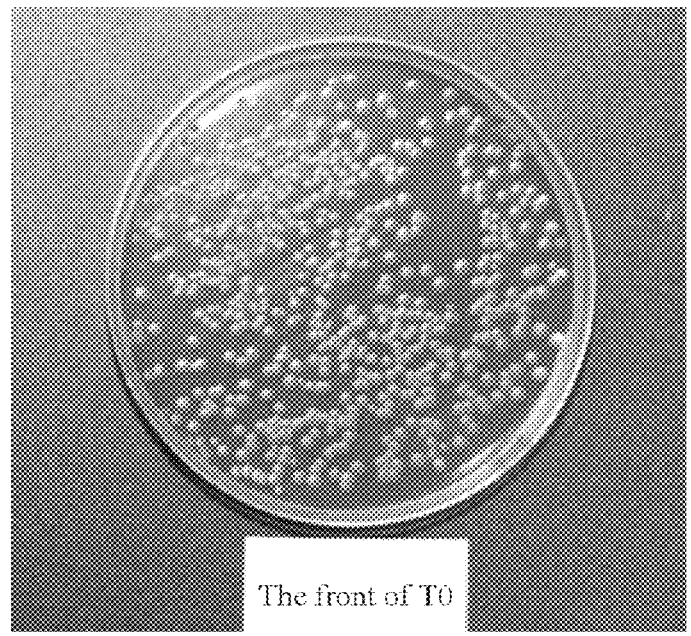
FIGS. 1A and 1B are the front view and the back view of the colonial morphology of the *Lactobacillus crispatus* 262-1 of the present invention, respectively.

The *Lactobacillus crispatus* 262-1 of the present invention is preserved in the China General Microbiological Culture Collection Center (CGMCC for short) on 22 Aug. 2012; the address of the preservation authority is the Institute of Microbiology, Chinese Academy of Sciences, No. 3 of Courtyard No. 1, West Beichen Road, Chaoyang District, Beijing City, the preservation registration number is CGMCC No. 6469, and the strain is classified and named as *Lactobacillus crispatus*.

DETAILED DESCRIPTION

Unless otherwise specified herein, the experimental methods used in the following embodiments are all conventional methods, and the used materials and reagents are all commercially available; and T0, T30 and T50 represent *Lactobacillus crispatus* of the 0th generation, the 30th generation and the 50th generation, respectively.

Preparation of the Bacteria Culture Medium:

1. Preparation of selective culture medium (Rogosa SL) of the *Lactobacillus crispatus* 262-1:

(1) preparing agar powders into a solution by 1.5 g/100 ml deionized water and sealing;

(2) putting the solution in a pressure cooker, and steaming under 1.0 MPa for 20 minutes; opening a super-clean bench for ultraviolet radiation for more than 20 minutes;

(3) taking out the agar solution when the pressure cooker has no pressure, and adding the *lactobacillus* selective culture medium (Rogosa SL Broth) in 5.97 g/100 ml agar solution;

(4) adding glacial acetic acid in 0.132 ml/100 ml agar solution, and boiling for 2.3 minutes in a micro-wave oven after being sealed;

(5) pouring the culture medium into a culture dish after the temperature of the culture medium lowers to the room temperature in an amount of 10 ml or 20 ml per culture dish based on the size of culture dish; and (6) conducting steps (3)-(5) in the super-clean bench, cooling the culture medium into agar gel, marking the name and preparation date of the culture medium, and putting same in a refrigerator at 4° C. for future use.

2. Preparation of broth solid medium (MRS):

(1) preparing agar powders into a solution by 1.59/100 ml deionized water;

(2) adding MRS Broth in 17.91 g/100 ml agar solution, and evenly mixing;

(3) putting the solution in the pressure cooker, and steaming at 1.0 MPa for 20 minutes; and (4) repeating the above-mentioned steps (5) and (6).

3. Preparation of broth liquid medium (MRS):

(1) adding the MRS Broth into the deionized water with a proportion of 17.91 g/100 ml;

(2) putting the solution in a pressure cooker, and steaming at 1.0 MPa for 20 minutes; and (3) taking out the solution when the pressure cooker has no pressure, distributing to EP tubes with 1.0 ml per tube, marking the name and preparation date of the culture medium, and putting same in a refrigerator at 4° C. for future use.

4. Preparation of hydrogen peroxide ($H_2O_2$) identification medium:

(1) repeating the preparation steps (1) to (4) of broth solid medium (MRS);

(2) taking out the solution after the pressure cooker has no pressure, slightly cooling, and adding TMB (the final concentration is 0.25 mg/ml) and HRP (the final concentration is 0.01 mg/ml) in super-clean bench when the medium is still in liquid state, mixing evenly; and (3) pouring the culture medium into a culture dish after the temperature of the culture medium lowers to the room temperature, cooling the culture medium into agar gel, marking the name and preparation date of the culture medium, and putting same in a refrigerator at 4° C. for future use.

Embodiment 1: The Separation, Inoculation, Purification and Enrichment Culture of the *Lactobacillus crispatus* 262-1 Flora I. Separation and inoculation of the *Lactobacillus crispatus* 262-1 flora: sample collection uses Port.A-Cd system from American BD company. 1/3 of the secretions of the subject's vaginal sidewall are gathered by using two sterile cotton swabs, and are inoculated in the culture dish provided with the prepared Rogosa SL culture medium at different concentrations within 24 hours. Information is marked. The culture dish is placed in a $CO_2$ aerogenesis bag of an anaerobic jar, and is then placed in an incubator at 37° C. for more than 48 h.

II. Purification and enrichment culture of the *Lactobacillus crispatus* 262-1 strain: counts are performed according to different morphologies (surface, edge and the like) and sizes of colonies, respectively; the colonies of the same morphology and the same size are marked as one kind, a few bacteria in the single colony are picked by an inoculating loop and are inoculated to the MRS solid medium by a "diagonal line method" to obtain a separated and purified single colony; and a few bacteria of the single colony on the MRS solid medium are picked by a bacterium toothpick, are inoculated to the MRS liquid medium, and are then placed in an incubator at 37° C. for anaerobic culture for 24 h-72 h. A new strain is selected and named as *Lactobacillus crispatus* 262-1.

Embodiment 2: Identification and Preservation of the Strain of the *Lactobacillus crispatus* 262-1

Figure 1B:
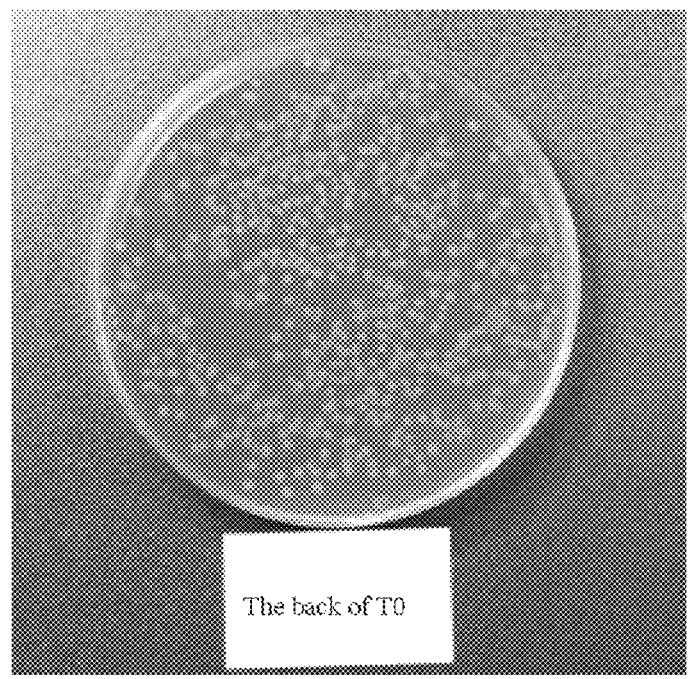
Figure 2:
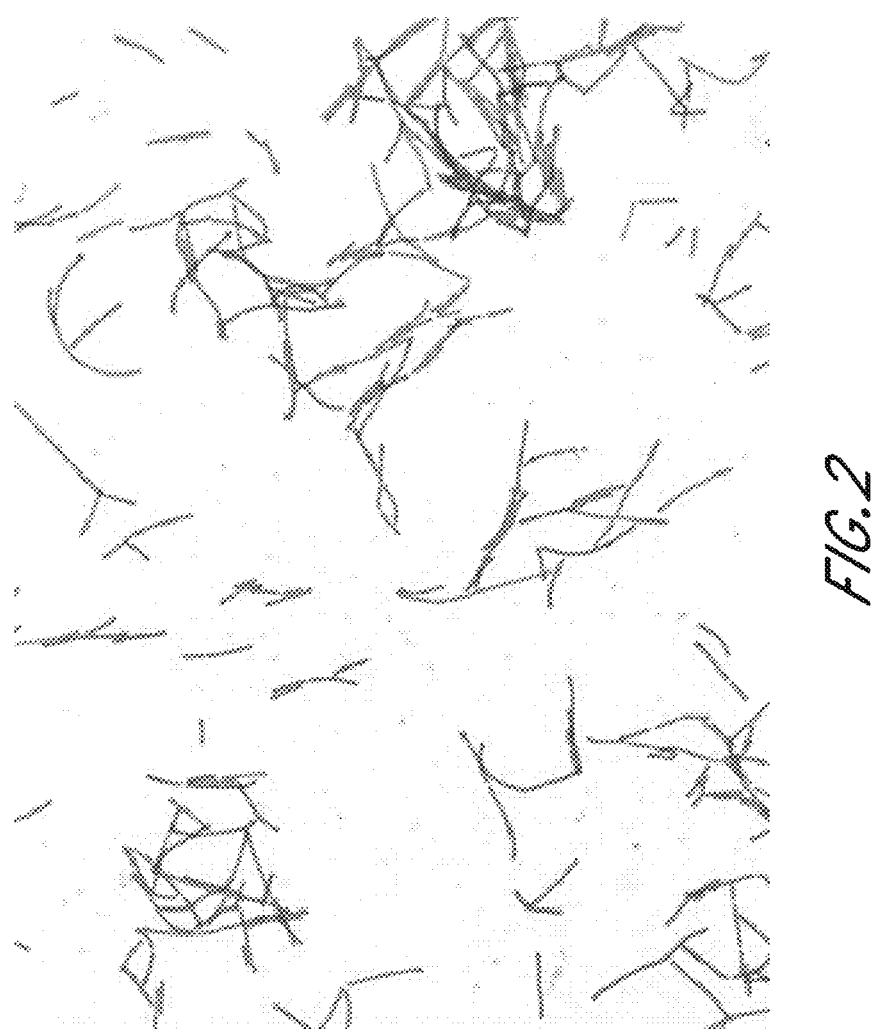
FIG. 2 is a Gram staining microscopic examination photo of the *Lactobacillus crispatus* 262-1 of the present invention.

I. Cultural character, staining microscopic examination and morphological feature: as shown in FIG. 1, the colony obtained after culture is circular and cloudy-white full in the middle, disperses around and is irregular; the pure culture smear of the colony is taken for Gram staining, and as shown in FIG. 2, the result presents Gram-positive, is short-rod-shaped, and can be linked to form a long chain; as shown in FIG. 3, the electron microscope analysis results are that: under an electron microscope, the strain is asporous, atrichous and acapsular, and the size of the strain is 26.824× 6.667 μm. Results show that: the separated strain is preliminarily judged as the *lactobacillus*.

II. 16SrDNA gene sequence identification: DNA extraction is performed with a bacterial genome DNA extraction kit and primer pairs 8F(5'-AGA GTT TGATCC TGG CTC AG-3') and 926R (5'-CCG TCAATT CCTTTR AGTTT-3') are adopted to perform PCR amplification, wherein R represents G or A, the PCR product is taken to perform gel electrophoresis to determine 16SrDNA gene fragment. The satisfactory result is obtaining a single band of PCR product clearly at 950 bp, shown in column T0 in FIG. 4. Purification and DNA sequencing are performed on the satisfactory PCR product, a Sanger sequencing method is adopted, the sequencing primer pair is 8F/926R, the sequencing instrument is ABI3730, the sequence similarity comparative analysis is carried out by the BLAST program in the GenBank database, and the species of lactobacillus is obtained according to the highest homology value which is greater than 98%. The partial sequence of 16SrDNA is shown in the sequence table SEQ ID NO:1, the 8F sequence is shown in the sequence table SEQ ID NO:4, and the 926R sequence is shown in the sequence table SEQ ID NO:5.

III. Physiological and biochemical properties: physiological and biochemical responses of the strain are tested via aesculin hydrolysis test, methyl red test (MR test), Voges-Proskauer test (VP test), indole test, triple sugar iron test, Kligler disaccharide iron test, urease test, Phenylalanine Deaminase (PD) test, amino acid decarboxylase test, gelatin liquefaction test, sodium malonate test, citrate experiment (citrate test), nitrate reduction test, litmus milk test and bacterial motility test, obtaining the following results: the Lactobacillus crispatus strain 262-1 can generate glucose and aescinbe by hydrolyzing aesculin; the MR test being positive indicates that metabolizable glucose produces organic acid; the VP test being negative indicates that metabolizable glucose does not produce pyruvic acid; the result of the indole test shows that tryptophan in peptone does not decomposed by the strain to produce indole; the triple sugar iron test indicates that metabolizable lactose glucose does not produce $H_2S$; the Kligler disaccharide iron test indicates that metabolizable lactose does not produce $H_2S$; the urease test, the PD test, the amino acid decarboxylase test and the gelatin liquefaction test are all negative, which indicates that the strain does not produce urease, phenylalanine deaminase, amino acid decarboxylase and gelatinases; the sodium malonate test, the citrate experiment (citrate test) and the nitrate reduction test are all negative, which indicates that the strain does not take sodium malonate as a carbon source, does not utilize citrate as a nitrogenous source and a carbon source, and does not reduce nitrate into nitrite; the litmus milk test observing that the strain can cause milk fermentation without solidifiction, which indicates that the strain grows vigorously without producing chymosin; and the bacterial motility test is negative. The biochemical identification is performed on the strain by the API 50 CHL lactobacillus identification system produced by Merieux company of France, the result shows that galactolipin, glucose, fructose, mannose, N-acetyl-glucosamine, amygdalin, arbutin, esculin, salicine, cellobiose, maltose, lactose, sucrose and starch are fermented at 24 h and 48 h, and are positive in the reaction; glycerine, eryth-rite, D-arabinose, L-arabinose, ribose, D-xylose, L-xylose, adonite, β-methyl-D-xyloside, sorbose, rhamnose, evonoside, inositol, mannitol, sorbierite, α-methyl-D-mannoside, α-methyl-D-glucoside, melibiose, synanthrin, melezitose, xylitol, geraniol, D-turanose, D-lyxose, D-tagatose, D-fucose, L-fucose, D-arabitol, L-arabinitol, gluconate, 2-keto-gluconate, 5-keto-gluconate are not fermented, and are negative in the reaction; trehalose, gossypose and glycogen are weak positive, the reaction is negative during substrate blank, and thus it is can be determined based on the biochemical map that biochemical characteristics of the strain correspond to the biochemical characteristic of the Lactobacillus crispatus.

IV. Preservation of the Lactobacillus crispatus 262-1: The Lactobacillus crispatus 262-1 of the present invention was preserved in the China General Microbiological Culture Collection Center (CGMCC for short) on 22 Aug. 2012; the address of the preservation authority is the Institute of Microbiology, Chinese Academy of Sciences, No. 3 of Courtyard No. 1, West Beichen Road, Chaoyang District, Beijing City, the preservation registration number is CGMCC No. 6469, and the strain is classified and named as Lactobacillus crispatus.

Embodiment 3: Determination of Metabolites of the Lactobacillus crispatus 262-1

I. Determination of lactic acid content in the metabolites of the Lactobacillus crispatus 262-1: the yield of D-lactic acid of this strain is determined to be 6.213 g/L using a D-lactic acid detection kit; and the content of the L-lactic acid is determined to be 3.789 g/L by a sensing analyzer. The results are presented in T0 group of data in the following Table 1.

TABLE 1 determined results of the lactic acid

| Samples | D-lactic acid (g/L) | L-lactic acid (g/L) |
|---|---|---|
| T0 | 6.213 | 3789 |
| T30 | 6.334 | 3.330 |
| T50 | 6.291 | 3.225 |

Figure 5:
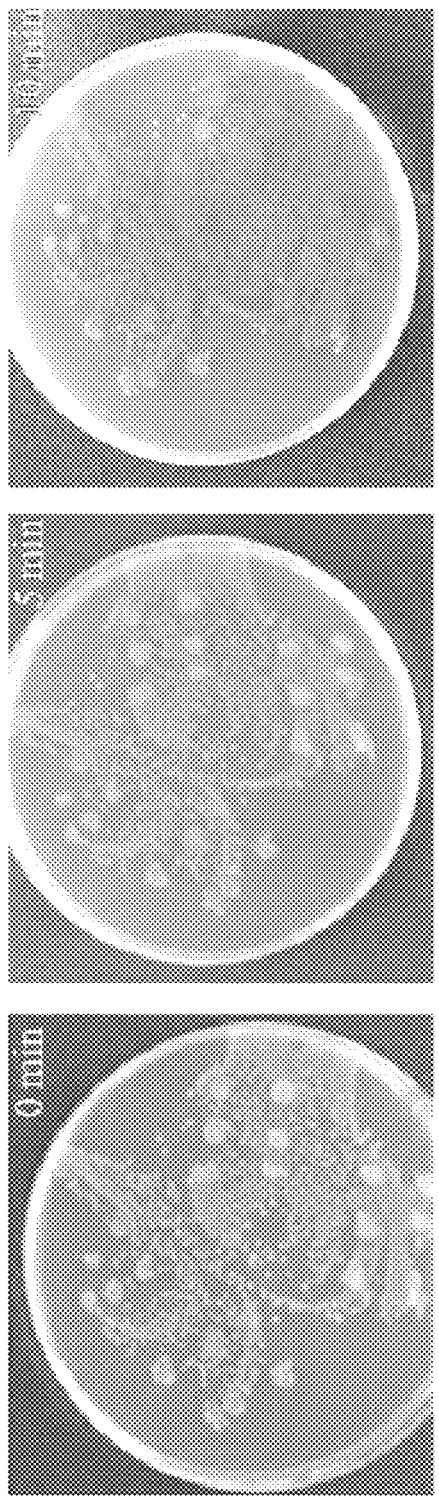
FIG. 5 is a picture showing the results obtained from the reaction of the *Lactobacillus crispatus* 262-1 of the present invention with hydrogen peroxide for 0 min, 5 min, and 10 min.

II. Determination of hydrogen peroxide content in the metabolites of Lactobacillus crispatus 262-1: semi-quantitative determination of hydrogen peroxide is performed by the peroxidase method of Mcgroarty et al. The separated and identified Lactobacillus crispatus is inoculated onto an MRS-TMB plate. The plate is taken out after anaerobic incubation at 37° C. for 24 hours, and the bacteria are exposed in the air. The colour of $H_2O_2$-producing Lactobacillus colonies will become blue, while the colour of colonies not producing $H_2O_2$ will not change. Semi-quantitation is performed on $H_2O_2$ according to the time of colour change, and the results are shown in FIG. 5, wherein a light blue colour appears in the colonies at the time of 5 min, while a large quantity of blue colour appears significantly at the time of 10 min. According to the criteria listed in Table 2, the metabolism of this strain produces hydrogen peroxide, with a semi-quantitative level of +++.

The above results show that the Lactobacillus crispatus 262-1 of the present invention can produce lactic acid and hydrogen peroxide, which contributes to maintain vaginal microecological balance.

TABLE 2 criteria for determining the $H_2O_2$ semi-quantitation

| Time of colour change for colony | Semi-quantitative level of $H_2O_2$ |
|---|---|
| <10 minutes | +++ |
| 10-<20 minutes | ++ |
| 20-30 minutes | + |
| >30 minutes or no colour change | − |

Embodiment 4: Antibiotic Sensitivity Test

According to the requirements on the antibiotic susceptibility test in the third general theory of micro-ecological viable bacterial product of pharmacopeia in 2010, the agar-diffusion paper-disc method is adopted to measure sensibility of the strains to the antibiotics, and the sensitivity level of the strains to the antibiotics is judged according to the sizes of the inhibition zones, the measurement results are as shown in Table 3, drug resistance of the *Lactobacillus crispatus* to flagyl (metronidazole), gentamicin, bacitracin and kanamycin, sensitivity of the *Lactobacillus crispatus* to ampicillin, ceftriaxone, chloromycetin, clindamycin, imipenem, erythromycin, piperacillin, tetracycline, azithromycin, amoxicillin and vancomycin, mediation of the *Lactobacillus crispatus* to penicillin and oxacillin are determined by the criteria for interpretation of scope of restraining fungi of the drug sensitive test disc method.

Embodiment 6: Test of Passage Stability of the *Lactobacillus crispatus* 262-1

In the embodiment, the stability of the *Lactobacillus crispatus* strain 262-1 after being passaged for 30 generations (T30) and 50 generations (T50) are examined from various aspects like growth characteristics, morphology, biochemical characteristics, metabolin composition, antibiotic sensitive characteristic, hereditary capacity and the toxicity test.

I. The separation and purification, the observation of colony morphology, staining microscopic examination and the detection method of biochemical characteristics of the *Lactobacillus crispatus* 262-1 are the same as those in the

TABLE 3 antibiotic sensitivity test results

| Antibiotics | Paper content/sheet | T0 Inhibition zone diameter/mm | Sensitivity determination | Reference bacterium | T30 Inhibition zone diameter/mm | T50 Inhibition zone diameter/mm |
|---|---|---|---|---|---|---|
| Ampicillin | 10 μg | 24 | Sensitivity | *Hemophilus* | 24 | 25 |
| Ceftriaxone | 30 μg | 29 | Sensitivity | *Hemophilus* | 31 | 30 |
| Chloramphenicol | 30 μg | 35 | Sensitivity | *Hemophilus* | 36 | 35 |
| Clindamycin | 2 μg | 35 | Sensitivity | *Hemophilus* | 37 | 36 |
| Imipenem | 10 μg | 40 | Sensitivity | *Hemophilus* | 40 | 40 |
| Gentamicin | 10 μg | 0 | Drug resistance | \ | 0 | 0 |
| Erythromycin | 15 μg | 36 | Sensitivity | *Streptococcus* | 41 | 39 |
| Bacitracin | 0.04 U | 0 | Drug resistance | \ | 0 | 0 |
| Penicillin | 10 IU | 24 | Mediation | Other *streptococcus* | 25 | 24 |
| oxacillin | 1 μg | 9 | Mediation | *Streptococcus pneumonia* | 10 | 9 |
| Piperacillin | 100 μg | 35 | Sensitivity | Other gram-negative bacteria | 37 | 35 |
| Amoxicillin | 10 μg | 20 | Sensitivity | *Hemophilus* | 24 | 23 |
| Vancomycin | 30 μg | 26 | Sensitivity | Other gram-positive coccis | 27 | 26 |
| Kanamycin | 30 μg | 0 | Drug resistance | \ | 0 | 0 |
| Metronidazole | 5 μg | 0 | Drug resistance | \ | 0 | 0 |
| Tetracycline | 30 μg | 38 | Sensitivity | *Hemophilus* | 40 | 39 |
| Azithromycin | 15 μg | 31 | Sensitivity | \ | 31 | 30 |

Note:
due to the fact that the drug sensitive disc diffusion method only has the determining criteria for the pathogenic bacteria and the *lactobacillus* is not listed therein, the listed determining criteria refer to the methods for determining the bacteria such as *hemophilus* and are set as three levels: sensitivity, mediation, and drug resistance.

Embodiment 5: Toxicity Test

Figure 6:
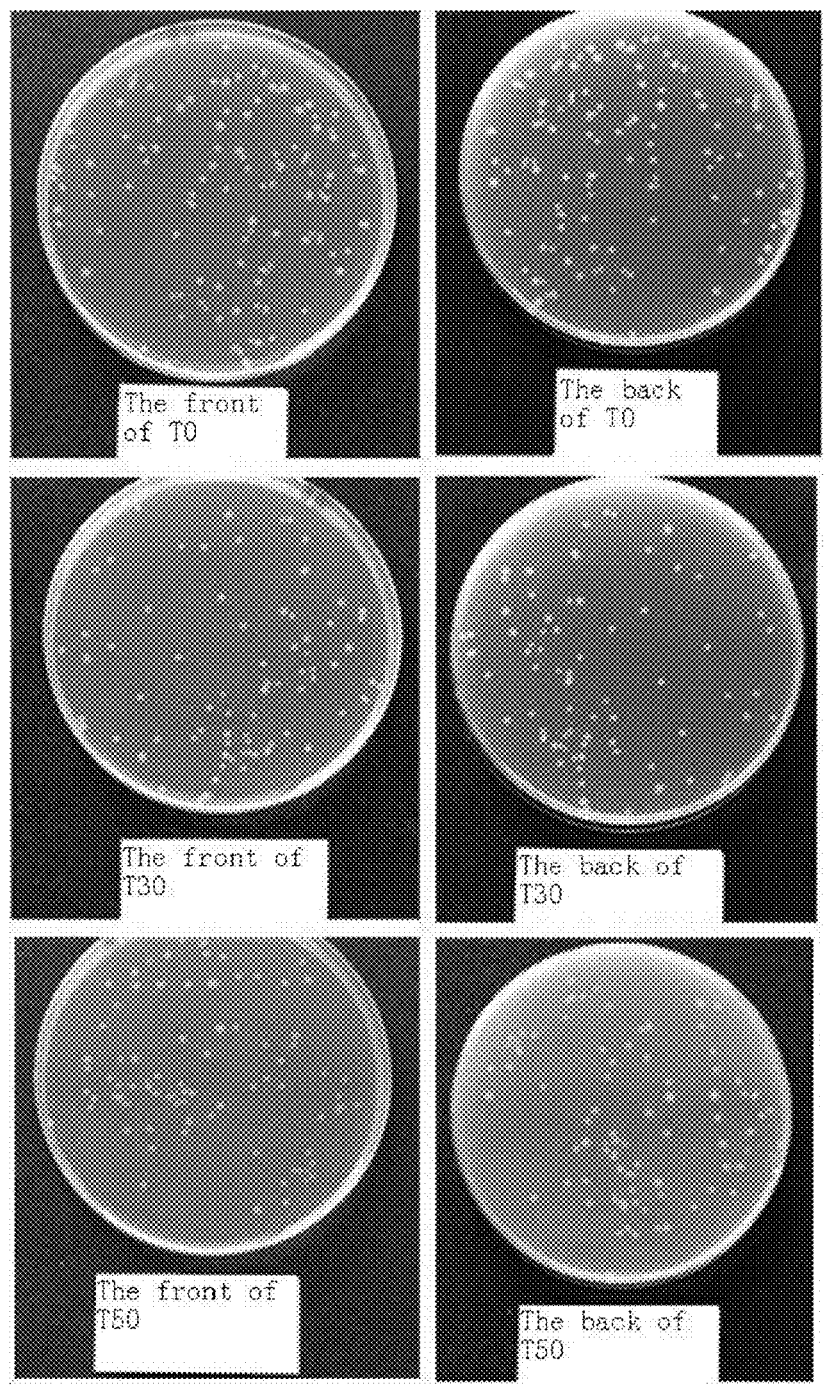
FIG. 6 is the front view and the back view of the colonial morphology of the *Lactobacillus crispatus* 262-1 T0, T30 and T50 of the present invention, respectively.
Figure 7:
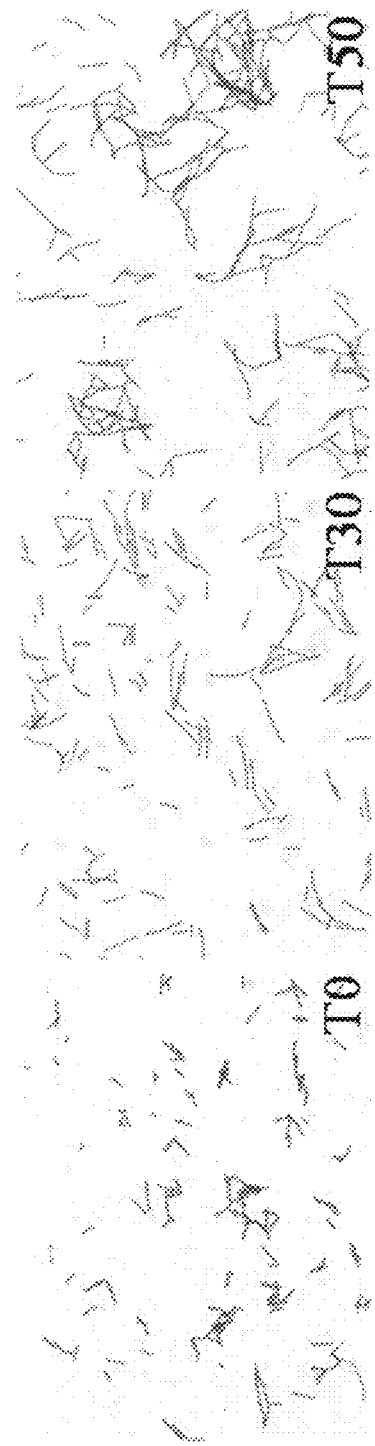
FIG. 7 is a Gram staining microscopic examination photo of the *Lactobacillus crispatus* 262-1 T0, T30 and T50 of the present invention.

Five Kunming mice (SPF level) are tested: 0.3 ml of fresh *Lactobacillus crispatus* 262-1 suspension (greater than $1 \times 10^9$ CFU/mouse) is injected into the abdomen of each mouse. According to the requirements of Chinese Pharmacopoeia 2010, the weight of each mouse is measured every day, and the changes in behaviors and physiology of each mouse before and after injection are observed and recorded. The results show that the weights of all the mice are increased within 7 days, and no obvious toxic symptom, abnormal behavior, or death occur. Thus, this strain is considered to be non-toxic strain.

first part of embodiments 1 and 2. Results show that the colonial morphology after passage is shown in FIG. 6, from which it can be seen that no significant change occurs, indicating that the passage is stable; Gram staining is represented as Gram-positive *bacillus*, and the staining microscopic examination photo is as shown in FIG. 7; results of the biochemical identification at 24 h and 48 h indicate that the biochemical reaction characteristics of various generations are consistent, and correspond to the biochemical characteristics of the *Lactobacillus crispatus*. The above results show that the biochemical characteristics of the strain correspond to the biochemical characteristic of the *Lactobacillus crispatus*, and the biochemical reaction characteristics of various generations are consistent.

Figure 4:
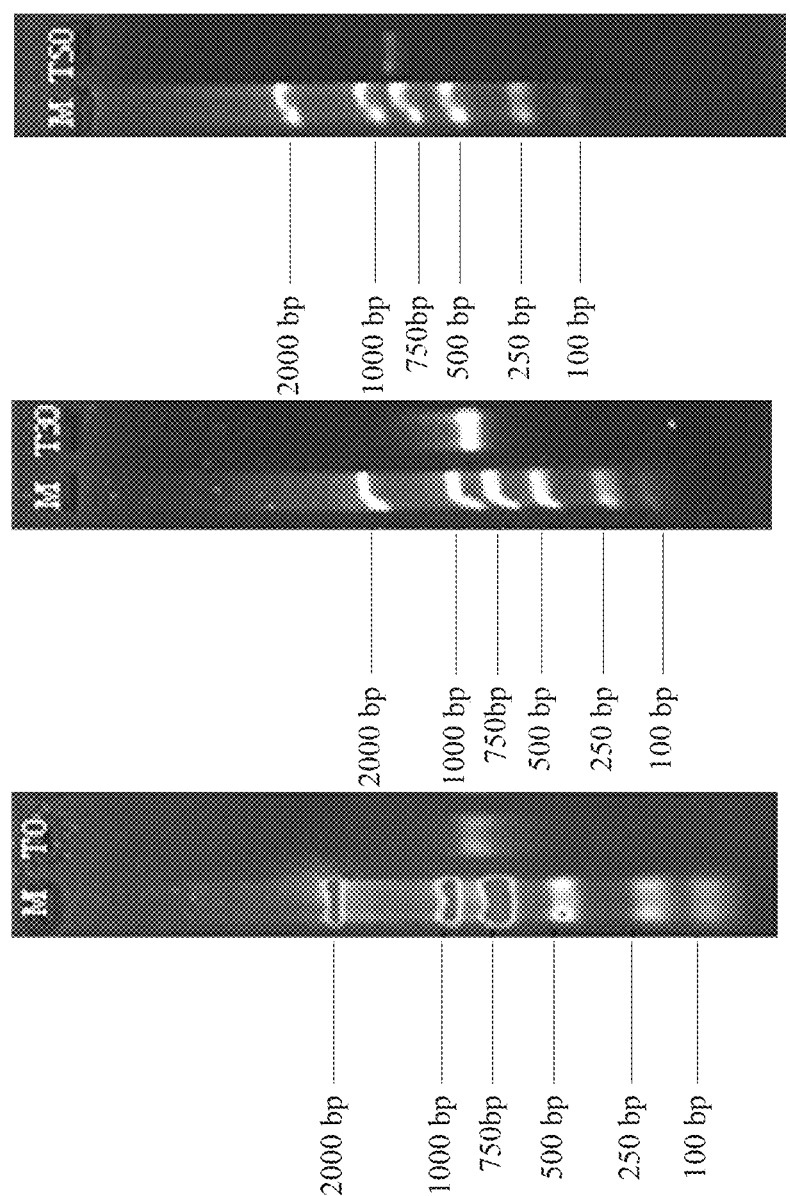
FIG. 4 is an electrophoretogram of 16SrDNA gene PCR amplified products of the *Lactobacillus crispatus* 262-1 T0, T30 and T50 of the present invention.

II. Genetic characteristic analysis: the method is the same as that in the second part of embodiment 2. A PCR amplification of 16S rRNA fragments is performed on the strain of the 0th generation (T0), the 30th generation (T30) and the 50th generation (T50) of the *Lactobacillus crispatus* 262-1, respectively. The products of the PCR amplification are analyzed by electrophoresis, as shown in FIG. 4, from which it can be seen that the target band is clear and single, its size is about 950 bp, the amplification is correct, and results of the three PCR amplifications on T0, T30 and T50 are consistent. The PCR amplification products of T0, T30 and T50 are sequenced, and the sequences are shown in sequence tables SEQ ID NO:1, SEQ ID NO:2 and SEQ ID NO:3, respectively. A comparison analysis is performed between the determined sequences and the known sequences in the GenBank database by using the BLAST tool in NCBI to be determined as the *Lactobacillus crispatus*.

Figure 8:
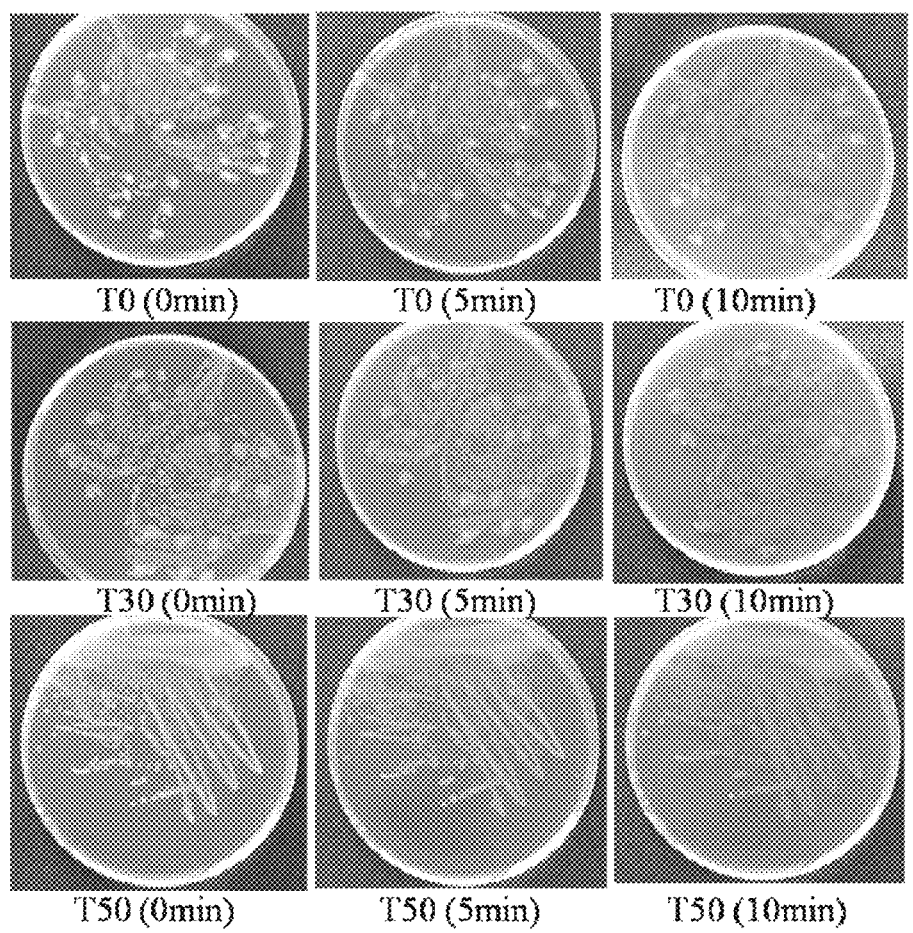
FIG. 8 is a picture showing the results obtained from the reaction of the *Lactobacillus crispatus* 262-1T0, T30 and T50 of the present invention with hydrogen peroxide for 0 min, 5 min, and 10 min.

III. Metabolite measurement: the method is the same as embodiment 3, the measured result of the lactic acid is as shown in Table 1, and the measured result of the hydrogen peroxide is as shown in FIG. 8. In FIG. 8, each generation of colony appears a light blue after 5 min, and a large amount of blue appears after 10 min, which proves that the hydrogen peroxide is produced during metabolism of strain, and the semi-quantitative level is +++.

IV. Antibiotic sensitivity test: the method is the same as embodiment 4, in which the agar-diffusion paper disc method is adopted to measure the sensitivity of the strain to the antibiotics; and drug resistance of the *Lactobacillus crispatus* to metronidazole, gentamicin, bacitracin and Kanamycin, sensitivity of the *Lactobacillus crispatus* to chloramphenicol, clindamycin, imipenem, erythromycin, piperacillin, tetracycline and azithromycin, and mediation of the *Lactobacillus crispatus* to ampicillin, ceftriaxone, penicillin, oxacillin, amoxicillin and vancomycin are determined by the criteria for interpretation of scope of restraining fungi of the drug sensitive test disc method, please see Table 3.

V. Toxicity test: the method is the same as embodiment 5, in which the toxicity test is performed on the T0, T30 and T50 generations of strains of the *Lactobacillus crispatus* 262-1 with the mice intra-peritoneal injection method, wherein the test concentration is greater than $10^9$ CFU/mouse. The results are as follows: all the tested mice are free of intoxication symptoms within 7 days, and the weights are all increased without animal death. Based on above results, this strain belongs to a non-toxic type strain according to "Supplementary Instructions of Technique Requirements for New Drug Pharmacology and Toxicology Research".

To sum up, the embodiment cultures the *Lactobacillus crispatus* 262-1 for multiple passages through the MRS culture medium, and discusses the impact of passage reproduction on the *Lactobacillus crispatus* 262-1 in the aspects of morphology, biochemistry, metabolite feature and hereditary characteristics, drug sensitive characteristics and toxicity test. Results show that: the passage within 50 generations cultured by MRS is identical with the initially separated strain in morphology, biochemistry, hereditary characteristics, metabolites and drug sensitive characteristics, and is stable.

Figure 9:
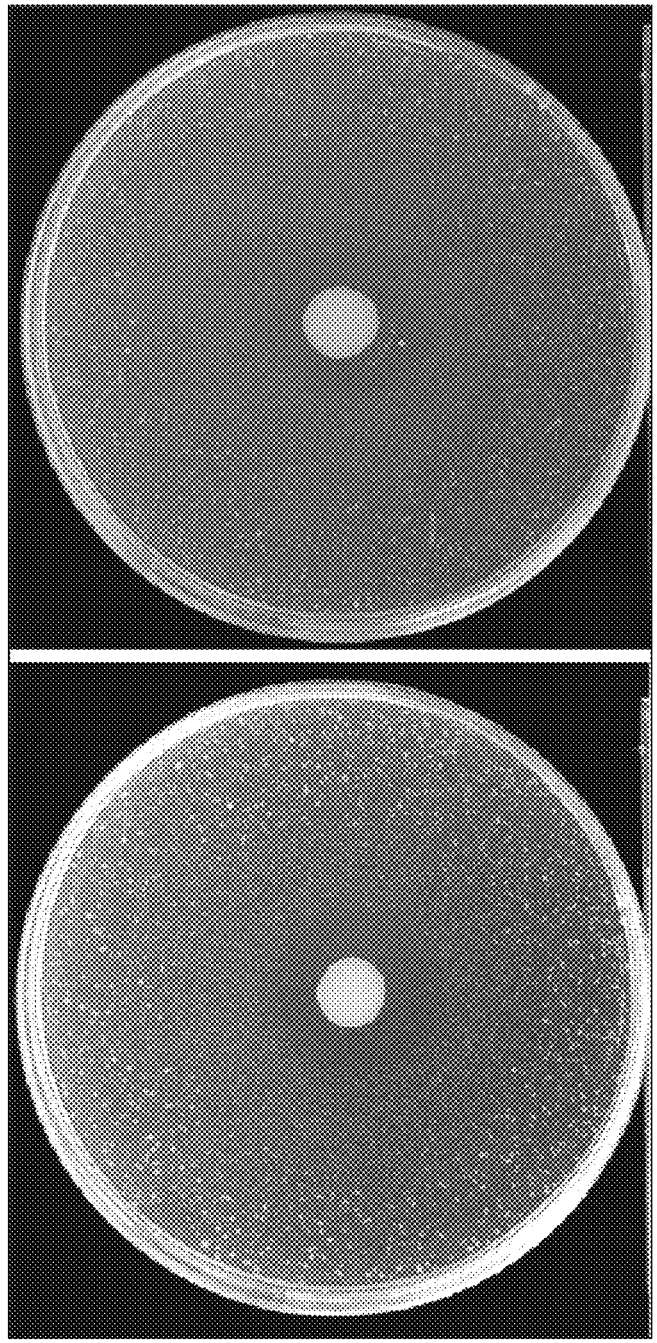
FIG. 9 is a photo showing antibacterial effects of the *Lactobacillus crispatus* 262-1 (left) and *Lactobacillus delbrueckii* (right) of the present invention on *Gardnerella vaginalis*.

Embodiment 7: Pharmacodynamic Experiments of the *Lactobacillus crispatus* 262-1 Strain I. In-vitro antibacterial experiments of the *Lactobacillus crispatus* 262-1 strain (1) The in-vitro inhibition experiment of *Lactobacillus crispatus* 262-1 and *Lactobacillus delbrueckii* on *Gardnerella vaginalis* is as follows: 5 μL of *Lactobacillus crispatus* 262-1 and 5 μL of *Lactobacillus delbrueckii* which are cultured overnight by 5% $CO_2$ at 37° C. are inoculated to MRS agar plates, respectively, and then are cultured in the anaerobic condition at 37° C. for 48 h; 100 μL of *Gardnerella vaginalis* is inoculated to 10 ml of BHI liquid medium, and is then cultured in the anaerobic condition at 37° C. for 48 h; 50 ml of soft BHI agar is sucked and added with 2.5 ml of horse serum and 1 ml of *Gardnerella vaginalis* suspension to be uniformly mixed, 5 ml of the mixture is sucked and tiled on the *lactobacillus* MRS agar plate which has been cultured for 48 h, and then the *lactobacillus* MRS agar plates are numbered respectively and cultured in the anaerobic condition at 37° C. for 48 h until an inhibition zone appears around the *lactobacillus*. The results are shown in FIG. 9, wherein the left figure shows the inhibition zone effect of the *Lactobacillus crispatus* 262-1, and the diameter of the inhibition zone is measured to be 21.68 mm by a vernier caliper, the right figure shows the inhibition zone effect of the *Lactobacillus delbrueckii*, and the diameter of the inhibition zone is measured to be 19.32 mm, and the conclusion is that the inhibition effect of the *Lactobacillus crispatus* 262-1 to *Gardnerella vaginalis* is better than that of the *Lactobacillus delbrueckii*.

Figure 10:
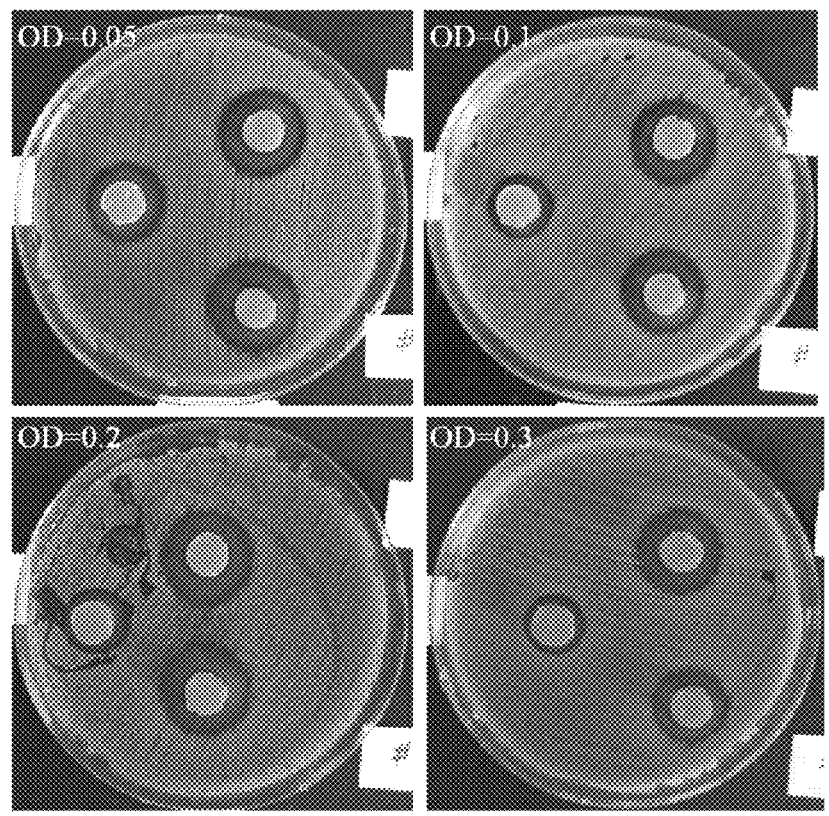
FIG. 10 is a photo showing antibacterial effects of the *Lactobacillus crispatus* 262-1 and *Lactobacillus delbrueckii* of the present invention on *Atopobium vaginae* under different concentrations ($OD_{600}$ is 0.05, 0.1, 0.2 and 0.3, respectively), wherein the two in the right column among the experiment culture dishes of different concentrations are photos showing antibacterial effects of the *Lactobacillus crispatus* 262-1, and the one in the left column is a photo showing antibacterial effect of the *Lactobacillus delbrueckii*.

(2) The in-vitro inhibition experiment of the *Lactobacillus crispatus* 262-1 and *Lactobacillus delbrueckii* on *Atopobium vaginae is as follows:* 5 μL of *Lactobacillus crispatus* 262-1 and 5 μL of *Lactobacillus delbrueckii* which are cultured overnight under 5% $CO_2$ at 37° C. are inoculated to MRS agar plates, respectively, and then are cultured in the anaerobic condition at 37° C. for 48 h; the *Atopobium vaginae* which has been cultured in the anaerobic condition at 37° C. is prepared into initial bacteria suspensions of different concentrations, and the values of $OD_{600}$ of the initial bacteria suspensions are 0.05, 0.1, 0.2 and 0.3, respectively. *Atopobium vaginae* suspensions of different concentrations are dipped and then uniformly coated on the whole surface of a Columbia blood agar culture medium; the cultured *Lactobacillus crispatus* 262-1 and *Lactobacillus delbrueckii* are pressed and punched, the bacterium cakes are taken out by tweezers and then placed upside down on the Columbia blood agar culture medium coated with *Atopobium vaginae*, and then the Columbia blood agar culture medium is cultured in the anaerobic condition at 37° C. for 48 h, and the inhibition zones are observed and recorded. The results are shown in Table 4 and FIG. 10, and a conclusion is obtained according to the figure and the measured size of the inhibition zone that the inhibition effect of the *Lactobacillus crispatus* 262-1 on *Atopobium vaginae* is obviously superior to that of the *Lactobacillus delbrueckii*; as the increase of the concentration of *Atopobium vaginae*, the inhibition effects of the *Lactobacillus crispatus* 262-1 on *Atopobium vaginae* are substantially constant, and the diameters of the inhibition zones are all about 20 mm; while the antibacterial ability of the *Lactobacillus delbrueckii* is reduced as the increase of the concentration of *Atopobium vaginae*.

TABLE 4

| | inhibition zone diameter (mm) | | | |
|---|---|---|---|---|
| Concentration | Lactobacillus crispatus 262-1 | | average value of Lactobacillus crispatus 262-1 | Lactobacillus delbrueckii |
| OD = 0.05 | 20.20 | 21.52 | 20.86 | 16.24 |
| OD = 0.1 | 20.40 | 20.90 | 20.65 | 14.26 |

TABLE 4-continued

| | | inhibition zone diameter (mm) | | |
|---|---|---|---|---|
| Concentration | Lactobacillus crispatus 262-1 | | average value of Lactobacillus crispatus 262-1 | Lactobacillus delbrueckii |
| OD = 0.2 | 22.26 | 21.86 | 22.06 | 14.34 |
| OD = 0.3 | 20.94 | 18.52 | 19.73 | 12.78 |

Figure 11:
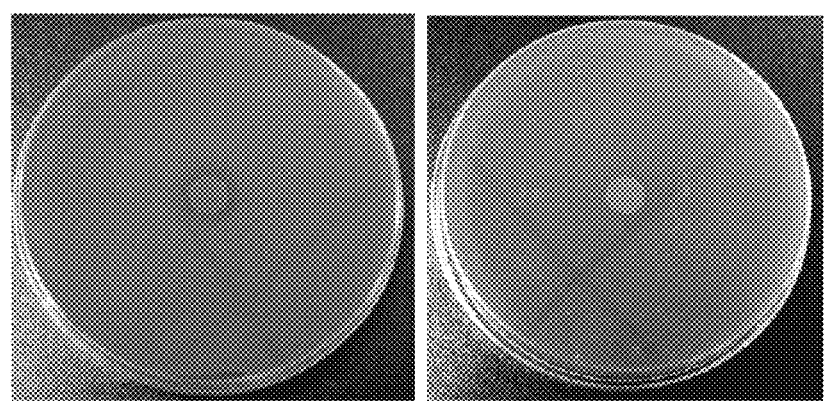
FIG. 11 is a photo showing antibacterial effects of the *Lactobacillus crispatus* 262-1 (left) and the *Lactobacillus delbrueckii* (right) of the present invention on *Candida albicans*.

(3) The in-vitro inhibition experiment of the *Lactobacillus crispatus* 262-1 and *Lactobacillus delbrueckii* on *Candida albicans*: 5 μL of the *Lactobacillus crispatus* 262-1 and 5 μL of fresh *Lactobacillus delbrueckii* solution are dibbled in an MRS agar medium, and then are cultured in the anaerobic condition at 37° C. for 48 h; 100 μL of fresh *Candida albicans* suspensions are uniformly mixed in 5 mL of soft YM agar (0.4% of agar, water bath at 50° C.), and the mixture is poured on *lactobacillus* MRS agar which has been cultured for 48 h, and then cultured in 5% $CO_2$ at 37° C. after being solidified until an inhibition zone appears around *lactobacillus*. The results are shown in FIG. 11, and the conclusion is that the inhibition zone of the *Lactobacillus crispatus* 262-1 on *Candida albicans* is obvious and clear, and inhibition effect thereof is apparently greater than that of the *Lactobacillus delbrueckii*.

(4) The in-vitro inhibition effect of the *Lactobacillus crispatus* 262-1 and *Lactobacillus delbrueckii* on pathogen *Staphylococcus aureus, Escherichia coli, Pseudomonas aeruginosa* and *salmonella*

Research method: 5 μL of the *Lactobacillus crispatus* 262-1 and 5 μL of fresh *Lactobacillus delbrueckii* solution are dibbled in an MRS agar medium, and then are anaerobically cultured in 5% $CO_2$ at 37° C. for 48 h; 100 μL of *Staphylococcus aureus*, 100 μL of *Pseudomonas aeruginosa*, 100 μL of *salmonella* and 100 μL of fresh *Escherichia coli* suspension are uniformly mixed in 5 mL of nutrient agar (0.4% of agar, water bath at 50° C.); the mixture is poured on the *lactobacillus* MRS agar medium which has been cultured for 48 h, and is incubated in 5% $CO_2$ at 37° C. after being solidified, until inhibition zone appears around *lactobacillus*. The results are shown in Table 5, and the conclusion is that the inhibition effects of *Lactobacillus crispatus* 262-1 on pathogen *Staphylococcus aureus, salmonella* and *Escherichia coli* are all superior to those of the *Lactobacillus delbrueckii*; the inhibition effects of the *Lactobacillus crispatus* 262-1 and *Lactobacillus delbrueckii* on *Pseudomonas aeruginosa* is the most obvious, and diameters of inhibition zone are all greater than 90 mm.

TABLE 5

| | inhibition zone diameter (mm) | |
|---|---|---|
| Pathogenic bacteria | Lactobacillus crispatus 262-1 | Lactobacillus delbrueckii |
| Escherichia coli | 50.0 | 43.0 |
| Staphylococcus aureus | 42.4 | 38.31 |
| salmonella | 51.33 | 48.10 |
| Pseudomonas aeruginosa | >90 | >90 |

II. The experiment for cell adhesive force: the adhesion performances of different *lactobacillus* are determined according to the number of *lactobacillus* attached on a monolayer of vaginal epithelial cell. The method comprises the following steps: taking human vaginal epithelial cells Vk2/E6E7 and human cervical carcinoma epithelial cells Hela; inoculating the cells on a 12-pore plate with the density of 450,000 per pore, and forming monolayer by the VK2/E6E7 after 48 hours; adding commercially available *lactobacillus* DJS and *Lactobacillus crispatus* 262-1 in each pore by different numbers of the CFU, respectively, and adhering for 4 hours, gently vibrating same on a shaker during adhesion process, and providing each group with two parallel experiments, respectively; after the adhesion is finished, splitting the cells with 1 ml of 0.05% tritonX-100 to prepare into bacteria suspension, diluting, taking 100 ul of bacteria suspension to be uniformly inoculated on the MRS agar medium plate, respectively; and after the anaerobic culture for 48 hours, calculating the number of clone of each plate.

The results show that: the adhesive rate of the *Lactobacillus crispatus* 262-1 at 4 h is 43.1% and 69.4%, respectively; and the adhesive rate of the commercially available *lactobacillus* DJS strain of the same kind at 4 h is 29.2% and 26%, respectively; and the adhesive force of the *Lactobacillus crispatus* 262-1 is higher than that of the commercially available *lactobacillus* DJS strain of the same kind.

III. Rhesus macaque vaginal colonization experiment

Five healthy animals are selected to carry out stratified random grouping based on the weight and are grouped into 2 groups with two animals in the control group (animal numbers are 1203, 1204) and three animals in the experimental group (animal numbers are 3211, 3212, 3222), wherein the animals for the experiment are female Chinese-origin Rhesus macaque (*Macaca mulatta*) provided by Suzhou Xishan ZhongKe Laboratory Animal Co., Ltd. The experimental method comprises the following steps.

Preparation of the *Lactobacillus crispatus* 262-1 for colonization: weighing lyophilized and dried powders of the *Lactobacillus crispatus* 262-1, so that the colonization amount is $10^8$; using the blank lyophilized adjuvant which is free of the *Lactobacillus crispatus* 262-1 for use; adding 0.7 mL of the MRS liquid medium respectively under aseptic condition, uniformly mixing and absorbing same by the vaginal administration device and implanting from the vagina.

Colonization modeling and sampling: after the menstruation of the Rhesus macaques with normal menstrual cycle can be observed, administrating azithromycin suppository (200 mg/Rhesus macaque) to the vagina for five consecutive days, then implanting the modeling bacteria for another 5 consecutive days; observing the animal vagina on a weekly basis by checking the colors, characters, and amounts of vaginal secretions as well as measuring pH value of the vaginal secretions; and sampling with two sterile polyester cotton swabs with one cotton swab being used for microscopic examination of the vaginal secretion cleanliness, and the other being used for flora analysis.

Separation and purification culture of vaginal bacteria: shaking the collected vaginal secretions in 2 mL of D-Hanks buffer solution and performing gradient dilution by phosphate buffer and then coating the product on Columbia blood agar, phenylethyl alcohol blood agar, MRS agar and *Candida albicans* selected agar plate, respectively; and culturing at 37° C. for 24-48 h under anaerobic condition; recording information such as single colonial morphology and quantity *haemolyticus*, and relining the Columbia blood agar plate to obtain the purified colony and performing biochemical and molecular identification.

Molecular biological method identification (16SrDNA gene sequence analysis): 16SrDNA sequence amplification, sequencing and analysis are performed on the separated and purified strain. First, an inoculating loop is used to pick the strain into a centrifuge tube containing 50 μL of PrepMan Ultra Sample Preparation Reagent and splitting in Dry Block Heater at 100° C. for 15 min before freezing preservation as DNA template at −20° C.; then, amplification on 16SrDNA fragments with sequences being SEQ ID NO:4 and SEQ ID NO:5 respectively is performed by using universal primer pair 8F/926R, wherein R represents G or A; each reagent is added in 50 μL of PCR reaction system. Name and volume of each reagent is 10×PCR Buffer 5 μL, dNTP (10 mM) 1 μL, MgCl$_2$ (50 mM) 0.5 μL, Platinum Taq DNA Polymerase (5 U) 0.2 μL, Primer 8F (10 μM) 1 μL, Primer 926R (10 μM) 1 μL, template (50 ng/μL) 1 μL, DNase/RNase-Free deionized water 39.3 μL. The PCR reaction conditions are set in the following order: PCR reaction consisting of 30 cycles of pre-denaturation at 94° C. for 2 min, denaturation at 94° C. for 1 min, annealing at 55° C. for 1 min, extension at 72° C. for 2 min, and extension at 72° C. for 10 min is performed. The obtained PCR product is tested by UV analyzer (loading solution prepared by the PCR product already includes stain) after electrophoresis through 1% agarose gel, and the obtained data is preserved.

The PCR amplification product identified as 16SrDNA fragment is sequenced after purifying the target fragment by gel cutting recovery method. Comparative analysis is performed on the measured 16SrDNA gene sequence by the BLAST tool of NCBI and the known sequences in GenBank database. If the comparative homology is greater than or equal to 98%, they are identified as the same species.

Experimental Result and Analysis

General observation of vaginal mucosa and secretions: observing on a week basis after implantation, wherein the result shows that there is no distinct abnormality detected on all experimental animal vaginal mucosa secretions.

Determination of the pH value of vaginal secretions: after implantation of the *Lactobacillus crispatus* 262-1, the pH values of most animal vaginal secretions in the experimental group are significantly lower than those of the control group, and are decreased significantly compared with that before the implantation. Determination results of pH values are shown in Table 6.

TABLE 6 determination results of pH values of secretions

| Animal number | Group | Before processing | After processing and before implantation | The first day after stopping implantation of *Lactobacillus crispatus* 262-1 | The eighth day after stopping implantation of *Lactobacillus crispatus* 262-1 | The fifteenth day after stopping implantation of *Lactobacillus crispatus* 262-1 | The twenty-second day after stopping implantation of *Lactobacillus crispatus* 262-1 | The twenty-ninth day after stopping implantation of *Lactobacillus crispatus* 262-1 |
|---|---|---|---|---|---|---|---|---|
| 1203 | Control | 7.0* | 6.5 | 5.5 | 6.5 | 6.5* | 6.1* | 6.5 |
| 1204 | Control | 4.4 | 7.0 | 7.0* | 7.0 | 4.7 | 5.8* | 7.0 |
| 3211 | Experimental group | 6.1 | 7.0* | 7.0 | 7.0 | 7.0 | 7.0 | 7.0 |
| 3212 | Experimental group | 7.0 | 7.0 | 4.7 | 4.7 | 4.7 | 4.7 | 4.4 |
| 3222 | Experimental group | 5.0 | 5.0 | 4.4 | 4.4 | 4.4 | 4.4 | 4.4 |

Note:

*marked part indicates that menstruation occurs to animal

Vaginal secretions cleanliness: the amounts of vaginal miscellaneous bacteria in the control group compared before and after implantation are significantly increased while cleanliness is reduced; and the experimental group shows that after the implantation of the *Lactobacillus crispatus* 262-1, the vaginal discharge cleanliness is significantly superior to that of control group. A different number of Gram-positive *bacillus vaginalis* can be seen, and cleanliness thereof is significantly higher than that of control group. Determination results of vaginal secretions cleanliness are shown in Table 7.

*Candida albicans* to observe the resistance effect of the *Lactobacillus crispatus* 262-1 to *Candida albicans*. After animal molding, bacterium suspension and vaginal Daktarin suppository are poured in vaginas once every day for totally 3 days. The observation results are as follows.

(1) After molding, the vaginal irrigation solution is taken out at the 5th and the 10th day, respectively; and colony counting is performed on *Candida albicans* and *Lactobacillus crispatus*, please see Table 8.

TABLE 7

Determination results of vaginal secretions cleanliness

| Animal number | Group | Before treatment | After treatment Before implantation | The first day after stopping implantation of Lactobacillus crispatus 262-1 | The eighth day after stopping implantation of Lactobacillus crispatus 262-1 | The fifteenth day after stopping implantation of Lactobacillus crispatus 262-1 | The twenty-second day after stopping implantation of Lactobacillus crispatus 262-1 | The twenty-ninth day after stopping implantation of Lactobacillus crispatus 262-1 |
|---|---|---|---|---|---|---|---|---|
| 1203 | Control | II* | II | II | II | II* | III* | III |
| 1204 | Control | I | I | I* | II | III | II* | II |
| 3211 | Experimental group | II | I* | I | I | I | I | II |
| 3212 | Experimental group | I | I | I | I | II | I | I |
| 3222 | Experimental group | III | III | II | II | II | II | III |

Note:
*marked part indicates that menstruation occurs to animal

Figure 12:
FIG. 12 is an electrophoretogram of the PCR amplified products of 16SrDNA fragments of some strains in the vaginal microbiota of Rhesus macaques whose vaginas have been colonized with the *Lactobacillus crispatus* 262-1 of the present invention.

Rhesus macaque vaginal microflora: 1% agarose gel electrophoresis detection is performed on the product of 16SrDNA fragments after PCR amplification; the result shows that one band is successfully amplified by most of bacterial strains, and the 16SrDNA amplification generated band of most samples are clear and meet the sequencing requirements. PCR amplification product electrophoresis for some of strains is shown in FIG. 12 with DL2000 as Marker. Fragment sizes thereof are 2000 bp, 1000 bp, 750 bp, 500 bp, 250 bp, 100 bp in descending order. Analysis shows that the size for 16SrDNA fragment is about 950 bp. Comparative analysis is performed on the measured 16SrDNA gene by the BLAST tool of NCBI and the known sequences in GenBank database. If the comparative homology is greater than or equal to 98%, they are identified as the same species.

Figure 13:
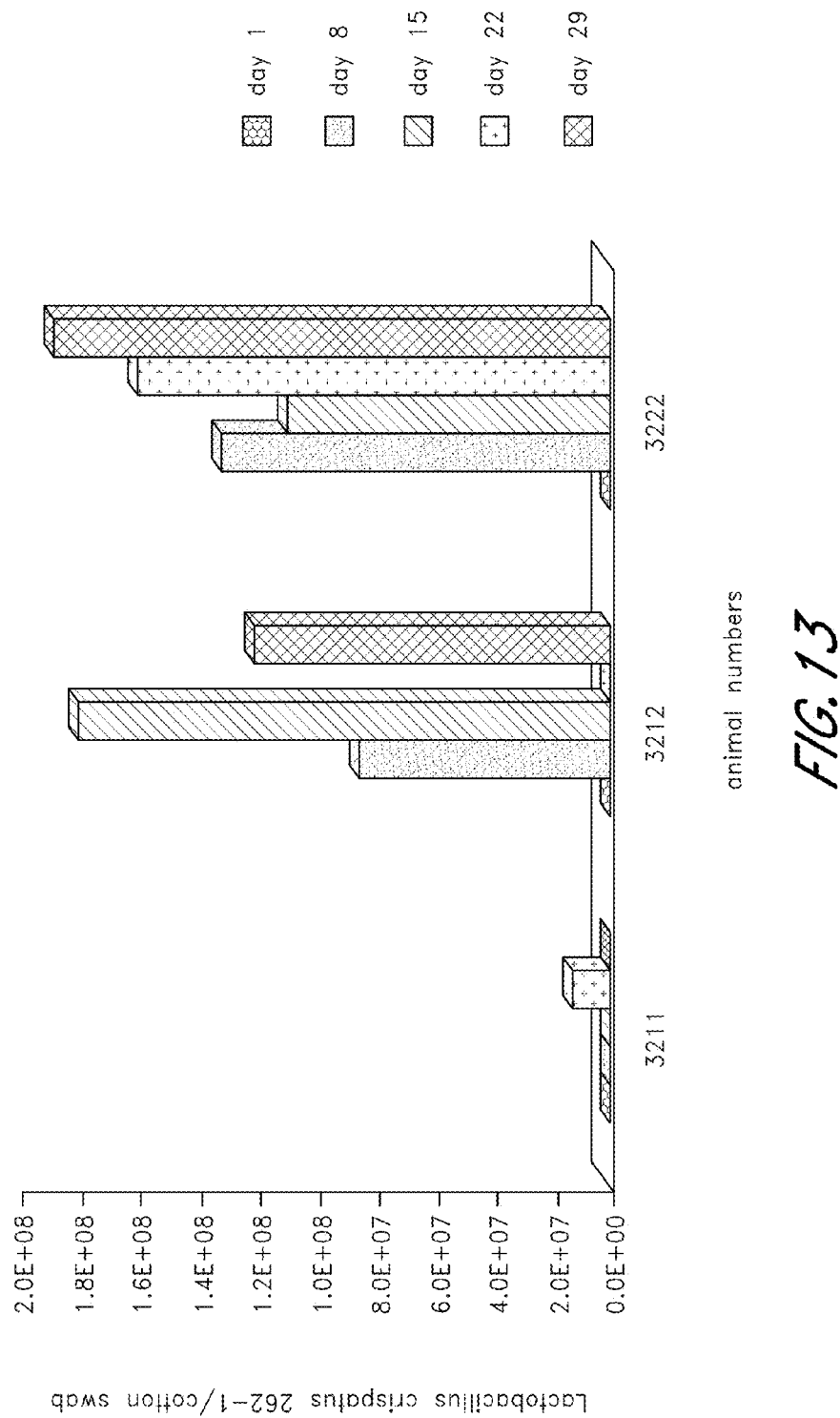

The *Lactobacillus crispatus* 262-1 for test is found in the vaginal secretions of the whole 3 animals of the experimental group through vaginal flora analysis, and the information about the separated *Lactobacillus crispatus* 262-1 for test is shown in FIG. 13. As can be seen from the FIG. 13, the *Lactobacillus crispatus* 262-1 for test is found in the vaginal secretions of all tested animals. Most of the *Lactobacillus crispatus* 262-1 will appear at and after the 8th day after colonization, which meets the rule. Moreover, the colonization effect is highly significant since the quantity is more than $10^7$/cotton swab. Therefore, it can be seen that the *Lactobacillus crispatus* 262-1 can be successfully colonized in the vaginas of China's Rhesus macaque when the initial colonization amount is $10^8$.

IV. Impact on *Candida albicans*' model in mice vaginas
Symbiontic experiment is performed in the vaginas of the cleaning-grade female ICR mice by the *lactobacillus* and

TABLE 8 colony counting results of all groups of irrigation solutions ($\times 10^6$ cfu)

| | 5 Days After Modeling | | 10 Days After Modeling | |
|---|---|---|---|---|
| Groups | Lactobacillus crispatus 262-1 ($\times 10^6$ cfu) | Candida albicans ($\times 10^6$ cfu) | Lactobacillus crispatus 262-1 ($\times 10^6$ cfu) | Candida albicans ($\times 10^6$ cfu) |
| Candida albicans + Lactobacillus crispatus 262-1 ($\times 10^6$ cfu) | 11.2 | 1.86 | 10.08 | 0.26 |
| Contrast of Candida albicans | 0 | 6.24 | 0 | 6.48 |
| Candida albicans + Daktarin suppository | 0 | 0.42 | 0 | 0.36 |

Conclusion: the bacterium amount carried by *Candida albicans* among the three experimental groups (*Candida albicans*+*Lactobacillus crispatus* 262-1, contrast group of *Candida albicans*, *Candida albicans*+Daktarin suppository group) is subjected to variance analysis, the result shows that during the first time period (5 d), in *Candida albicans*+*Lactobacillus crispatus* 262-1 group and contrast group of *Candida albicans*, $P>0.05$ and there is no statistical difference; in *Candida albicans*+Daktarin suppository group and *Candida albicans*+*Lactobacillus crispatus* 262-1 group as well as contrast group of *Candida albicans*, $P<0.05$ and there is statistical difference; and in *Candida albicans*+

Daktarin suppository group and *Candida albicans*+*Lactobacillus crispatus* 262-1 group, P=0.033, and there is also statistical difference. During the second period (10 d), there is no statistical difference between *Candida albicans*+*Lactobacillus crispatus* 262-1 group and *Candida albicans*+ Daktarin suppository group, suggesting that the *Lactobacillus crispatus* 262-1 has curing effects of significantly resisting the *Candida albicans*.

(2) Periodic acid schiff staining (PAS) is performed on experiment sample pathological section to observe the specially stained results of the *Candida albicans*, please see Table 9.

TABLE 9 vaginal *Candida albicans* infection status of experimental animals in each experimental group (on an individual animal basis)

| Experiment group | Number of samples | PAS specific stain* (status of fungus) | | | |
|---|---|---|---|---|---|
| | | +++* | ++ | + | − |
| A. *Candida albicans* + *Lactobacillus crispatus* 262-1 group | 10 | 0 | 5 | 3 | 2 |
| B. control group of *Candida albicans* | 10 | 7 | 3 | 0 | 0 |
| D. *Candida albicans* + Daktarin suppository group | 10 | 0 | 2 | 4 | 4 |

Histopathological specially stained result indicates that the result of *Candida albicans*+*Lactobacillus crispatus* 262-1 group is similar to that of *Candida albicans*+Daktarin suppository group. This experimental result indicates that the *Lactobacillus crispatus* 262-1 can be used as a supplementary means for the treatment of vaginal diseases caused by *Candida albicans*.

Embodiment 8: Lyophilization of the *Lactobacillus crispatus* 262-1 and Stability of Lyophilized Powder In order to test the survival rate of the *Lactobacillus crispatus* 262-1 under fermentation and lyophilization conditions, the *Lactobacillus crispatus* 262-1 is grown in the modified MRS medium with pH value of 6.0, and a BioFlo 110 fermentation tank with a volume of 1 liter (New Brunswick Scientific) is used for fermentation. Bacteria are collected in the early period of stationary phase, wherein viable count is $1.0\text{-}1.5\times10^9$ CFU/ml, and the viable bacteria account for more than 90% of the total bacteria count. Bacteria are collected by means of centrifugal separation, and are mixed with lyophilization protectant (comprising xylitol, ascorbate, α-tocopherol and phosphate buffer and so on) after washing with phosphate buffer. Then, the mixture is palced in a Virtis Advantage freeze dryer for lyophilization. The sample is frozen at −40° C. for 1-20 hours, and dried at −40° C. under vacuum for 2-60 hours and then dried at 25° C. for 10-40 hours. Lyophilized powders are distributed in the aluminum foil bag with drying agent, and are stored at 4° C. and room temperature (25° C.). The total bacteria count and viable count are respectively measured by means of plate count and CFU measurement on the 0th, 30th and 180th day. Every gram of lyophilized powder in the initial *Lactobacillus crispatus* 262-1 contains as high as 34 billion viable bacteria ($3.4\times10^{10}$ cfu/g), which have the optimal storage stability at 4° C. After being stored at 4° C. for 6 months, 70.6% of initial viable count is retained as shown in Table 10.

TABLE 10 result of stability test of 6 months of *Lactobacillus crispatus* 262-1 lyophilized powder

| Condition | Total bacteria count per gram of lyophilized powder | Total bacteria count per gram of lyophilized powder | Viable bacteria rate/% |
|---|---|---|---|
| 0 month | $8.5 \times 10^{10}$ | $3.4 \times 10^{10}$ | 40.0 |
| 1 month, 4° C. | $8.4 \times 10^{10}$ | $3.1 \times 10^{10}$ | 36.9 |
| 1 month, room temperature | $8.1 \times 10^{10}$ | $1.8 \times 10^{10}$ | 22.2 |
| 6 months, 4° C. | $7.8 \times 10^{10}$ | $2.4 \times 10^{10}$ | 30.8 |
| 6 months, room temperature | $4.0 \times 10^{10}$ | $5.8 \times 10^{9}$ | 14.5 |

Embodiment 9: Preparation of the *Lactobacillus crispatus* 262-1 Capsule-Type Inoculum, Steps are as Follows (1) the frozen liquid *Lactobacillus crispatus* 262-1 seeds or original seeds of −70° C. are fetched and inoculated in 30 mL of MRS liquid medium, which is cultured in 5% $CO_2$ at 37° C. for 24 h;

(2) appropriate amount of bacteria liquid in (1) is fetched and added into 500 ml of fermentation culture solution, which is cultured in 5% $CO_2$ at 37° C. for 24 h;

(3) appropriate amount of fermentation culture solution is added in a 50 L of fermentation tank, and is sterilized under high pressure for 20 min;

(4) the bacteria liquid is inoculated in the fermentation culture solution in the fermentation tank, the concentration of the starting bacteria liquid is controlled as $OD_{600}$ value about 0.4, pH 6.0, appropriate amount of nitrogen is added at 37° C., and fermentation time is about 8-10 h;

(5) the fermentation product is centrifugally collected, the microorganism lyophilized protective liquid is added to prepare into bacteria suspension, and bacteria concentration is determined and adjusted at $1.0\text{-}1.5\times10^9$ CFU/ml; and (6) the above-mentioned bacteria suspension is transferred onto the lyophilization plate of lyophilization drier which is started to dry in vacuum for 48 hours, after the drying is finished, the bacteria suspension is pulverized and filled into capsule.

In the concrete implementation, the cultivation scale can be expanded or reduced accordingly according to the volume of the product to be obtained.

Embodiment 10: Preparation of the *Lactobacillus crispatus* 262-1 Liquid-Type Inoculum The preparation steps are the same as steps (1)-(5) in embodiment 9; and the difference with embodiment 9 is that the culture solution obtained through fermentation in step (5) is discharged from the tank, and is directly distributed into liquid dosage form by using plastic packaging barrels or packaging bottle.

In view of the above data, it can be seen that the *Lactobacillus crispatus* 262-1 is stable in passage, is consistent in morphology, biochemical properties, hereditary characteristic, metabolin and drug sensitivity characteristic for each generation, and can generate lactic acid and hydrogen peroxide, which contribute to maintain micro-ecological balance in vaginas; it is non-toxic and safe, and has good biocompatibility; it has good inhibition effect on *Gardnerella vaginalis, Atopobium vaginae, Candida albicans* and pathogenic bacteria *Staphylococcus aureus, Escherichia* coli, *Pseudomonas aeruginosa* and *salmonella* in vagina; it has strong vaginal colonization ability and good improvement result on vaginal microenvironments such as pH and cleanness; and it can obviously inhibit *Candida albicans* and has similar therapeutic effect to Daktarin suppository, which prompts that the *Lactobacillus crispatus* can be used as the supplementary means for the treatment of vaginal diseases due to *Candida albicans*; the inoculant, made by taking the strains as active ingredients, has high bacteria rate, good stability, and convenient storage.

These pieces of data show that the addition of the *Lactobacillus crispatus* 262-1 or inoculum made thereby to the cosmetic product or disinfectant for pudendum use, and to the related product in contact with vagina, such as material or coating of medical instruments, enables the *Lactobacillus crispatus* 262-1 to improve and regulate vaginal microenvironment, and inhibit vaginal pathogenic bacteria, and meanwhile, the *Lactobacillus crispatus* 262-1 has good biocompatibility and is safe and non-toxic, plays an important role in female pudendum sanitation and care, and further has great application potential in developing a product which is both sanitation guaranteed and good for women's health.

What is claimed is:

1. A method for inhibiting a vaginal pathogenic microorganism, comprising contacting a composition comprising an isolated *Lactobacillus crispatus* strain named 262-1 with a subject, wherein the *Lactobacillus crispatus* strain named 262-1 is deposited in the China General Microbiological Culture Collection Center under accession number of CGMCC No. 6469, thereby inhibiting said vaginal pathogenic microorganism.

2. The method according to claim 1, wherein the vaginal pathogenic microorganism is selected from the group consisting of *Gardnerella vaginalis, Candida albicans, Atopobium vaginae, Staphylococcus aureus, Escherichia coli, Pseudomonas*, and *Pseudomonas salmonella*.

3. The method according to claim 1, wherein the subject suffers from a vaginal disease.

4. The method according to claim 3, wherein the vaginal disease is vulvovaginal candidasis, trichomonas vaginitis, senile vaginitis, non-specific vaginal infection or mixed vaginal infection.

5. The method according to claim 1, wherein contacting the composition comprising the isolated *Lactobacillus crispatus* strain named 262-1 with the subject comprises contacting a medical instrument comprising the isolated *Lactobacillus crispatus* strain named 262-1 with the subject.

6. The method according to claim 1, wherein the composition is a female vaginal nursing solution, a female vaginal nursing cream, a female vaginal nursing paste, a female vaginal nursing mask, or a body wash.

7. The method according to claim 1, wherein the composition is in a liquid state, a solid state, or a gel state.

8. The method according to claim 2, wherein the vaginal pathogenic microorganism is comprise *Gardnerella vaginalis* or *Candida albicans*.

9. The method according to claim 1, wherein the *Lactobacillus crispatus* strain named 262-1 comprises a 16S rDNA sequence having at least 98% sequence identity to the sequence of SEQ ID NO: 1.

10. The method according to claim 8, wherein the *Lactobacillus crispatus* strain named 262-1 comprises a 16S rDNA sequence having at least 99% sequence identity to the sequence of SEQ ID NO: 1.

11. The method according to claim 9, wherein the *Lactobacillus crispatus* strain named 262-1 comprises a 16S rDNA sequence having 100% sequence identity to the sequence of SEQ ID NO: 1.

12. The method according to claim 1, wherein the *Lactobacillus crispatus* strain named 262-1 exhibits an adhesion force to vaginal epithelial cell at a rate of at least 43.1% after 4 hours.

13. The method according to claim 1, wherein the vaginal pathogenic microorganism causes a vaginal disease selected from the group consisting of vulvovaginal candidasis, trichomonas vaginitis, senile vaginitis, non-specific vaginal infection, and mixed vaginal infection.

14. The method according to claim 1, wherein the *Lactobacillus crispatus* 262-1 strain regulates vaginal flora balance.

15. The method according to claim 5, wherein the medical instrument is selected from the group consisting of colposcopes, gynecological self-checking colposcopes, vaginal dilators, vaginal speculums, therapeutic apparatuses for gynecological pelvic inflammatory diseases, gynecological irrigators, and antibacterial devices for gynecological external use.

* * * * *

UNITED STATES PATENT AND TRADEMARK OFFICE
CERTIFICATE OF CORRECTION

PATENT NO. : 9,937,214 B2
APPLICATION NO. : 15/034503
DATED : April 10, 2018
INVENTOR(S) : Yang Liu It is certified that error appears in the above-identified patent and that said Letters Patent is hereby corrected as shown below:

In the Specification

In Column 1, Line 16 (Approx.), above "BACKGROUND" insert --SEQUENCE LISTING
The instant application contains a Sequence Listing which has been submitted in ASCII format via EFS-Web and is hereby incorporated by reference in its entirety. Said ASCII copy, created on September 30, 2016, is named SJUZ003-001APC_Sequencelisting.txt and is 4.41 Kilobytes in size. The information in the electronic format of the Sequence Listing is incorporated herein by reference in its entirety.--.

In Column 7, Line 43, change "solidifiction," to --solidification,--.

In Column 7, Line 49, change "galactolipin," to --galactolipid,--.

In Columns 9-10, Line 7 (Table 3), change "Hemophilus" to --Haemophilus--.

In Columns 9-10, Line 8 (Table 3), change "Hemophilus" to --Haemophilus--.

In Columns 9-10, Line 9 (Table 3), change "Hemophilus" to --Haemophilus--.

In Columns 9-10, Line 10 (Table 3), change "Hemophilus" to --Haemophilus--.

In Columns 9-10, Line 11 (Table 3), change "Hemophilus" to --Haemophilus--.

In Columns 9-10, Line 24 (Table 3), change "Hemophilus" to --Haemophilus--.

In Columns 9-10, Line 32 (Table 3), change "Hemophilus" to --Haemophilus--.

In Columns 9-10, Line 37 (Table 3), change "hemophilus" to --haemophilus--.

In Column 10, Line 8, change "metabolin" to --metabolic--.

Signed and Sealed this
Twenty-ninth Day of October, 2019

Andrei Iancu
*Director of the United States Patent and Trademark Office*

In Column 17, Line 66, change "Symbiontic" to --Symbiotic--.

In Column 19, Line 54, change "palced" to --placed--.

In Column 20, Line 61, change "metabolin" to --metabolic--.

In the Claims

In Column 25, Line 17, Claim 4, change "candidasis," to --candidiasis,--.

In Column 25, Line 32, Claim 8, change "is comprise" to --is--.

In Column 26, Line 20, Claim 13, change "candidasis," to --candidiasis,--.

SEQUENCE LISTING

<160> NUMBER OF SEQ ID NOS: 5

<210> SEQ ID NO 1
<211> LENGTH: 919
<212> TYPE: DNA
<213> ORGANISM: Lactobacillus Crispatus

<400> SEQUENCE: 1

```
cttgagtttc aaccttgcgg tcgtactccc caggcggagt gcttaatgcg ttagctgcag      60
cactgagagg cggaaacctc ccaacactta gcactcatcg tttacggcat ggactaccag     120
ggtatctaat cctgttcgct acccatgctt tcgagcctca gcgtcagttg cagaccagag     180
agccgccttc gccactggtg ttcttccata tatctacgca ttccaccgct acacatggag     240
ttccactctc ctcttctgca ctcaagaaaa acagtttccg atgcagttcc tcggttaagc     300
cgagggcttt cacatcagac ttattcttcc gcctgcgctc gctttacgcc caataaatcc     360
ggacaacgct tgccacctac gtattaccgc ggctgctggc acgtagttag ccgtgacttt     420
ctggttgatt accgtcaaat aaaggccagt tactacctct atccttcttc accaacaaca     480
gagctttacg atccgaaaac cttcttcact cacgcggcgt tgctccatca gacttgcgtc     540
cattgtggaa gattccctac tgctgcctcc cgtaggagtt tgggccgtgt ctcagtccca     600
atgtggccga tcagtctctc aactcggcta tgcatcatcg ccttggtaag cctttacctt     660
accaactagc taatgcaccg cggggccatc ccatagcgac agcttacgcc gccttttaaa     720
agctgatcat gcgatctgct ttcttatccg gtattagcac ctgtttccaa gtggtatccc     780
agactatggg gcaggttccc cacgtgttac tcacccatcc gccgctcgct ttcctaacgt     840
cattaccgaa gtaaatctgt tagttccgct cgctcgactt gcatgtatta ggcacgccgc     900
cagcgttcgt cctgagcag                                                 919
```

<210> SEQ ID NO 2
<211> LENGTH: 898
<212> TYPE: DNA
<213> ORGANISM: Lactobacillus Crispatus

<400> SEQUENCE: 2

```
cgggcgggtg ctatactgca gtcgagcgag cggaactaac agatttactt cggtaatgac      60
gttaggaaag cgagcggcgg atgggtgagt aacacgtggg gaacctgccc catagtctgg     120
gataccactt ggaaacaggt gctaataccg gataagaaag cagatcgcat gatcagcttt     180
taaaaggcgg cgtaagctgt cgctatggga tggccccgcg gtgcattagc tagttggtaa     240
ggtaaaggct taccaaggcg atgatgcata gccgagttga gagactgatc ggccacattg     300
ggactgagac acggcccaaa ctcctacggg aggcagcagt agggaatctt ccacaatgga     360
cgcaagtctg atggagcaac gccgcgtgag tgaagaaggt tttcggatcg taaagctctg     420
```

```
ttgttggtga agaaggatag aggtagtaac tggcctttat ttgacggtaa tcaaccagaa    480
agtcacggct aactacgtgc cagcagccgc ggtaatacgt aggtggcaag cgttgtccgg    540
atttattggg cgtaaagcga gcgcaggcgg aagaataagt ctgatgtgaa agccctcggc    600
ttaaccgagg aactgcatcg gaaactgttt ttcttgagtg cagaagagga gagtggaact    660
ccatgtgtag cggtggaatg cgtagatata tggaagaaca ccagtggcga aggcggctct    720
ctggtctgca actgacgctg aggctcgaaa gcatgggtag cgaacaggat tagataccct    780
ggtagtccat gccgtaaacg atgagtgcta agtgttggga ggtttccgcc tctcagtgct    840
gcagctaacg cattaagcac tccgcctggg gagtacgacc gcaaggttga actcaggg     898
```

<210> SEQ ID NO 3
<211> LENGTH: 897
<212> TYPE: DNA
<213> ORGANISM: Lactobacillus Crispatus

<400> SEQUENCE: 3

```
ccattcgctg ctataatgca gtcgagcgag cggaactaac agatttactt cggtaatgac    60
gttaggaaag cgagcggcgg atgggtgagt aacacgtggg gaacctgccc catagtctgg   120
gataccactt ggaaacaggt gctaataccg gataagaaag cagatcgcat gatcagcttt   180
taaaaggcgg cgtaagctgt cgctatggga tggccccgcg gtgcattagc tagttggtaa   240
ggtaaaggct taccaaggcg atgatgcata gccgagttga gagactgatc ggccacattg   300
ggactgagac acggcccaaa ctcctacggg aggcagcagt agggaatctt ccacaatgga   360
cgcaagtctg atggagcaac gccgcgtgag tgaagaaggt tttcggatcg taaagctctg   420
ttgttggtga agaaggatag aggtagtaac tggcctttat ttgacggtaa tcaaccagaa   480
agtcacggct aactacgtgc cagcagccgc ggtaatacgt aggtggcaag cgttgtccgg   540
atttattggg cgtaaagcga gcgcaggcgg aagaataagt ctgatgtgaa agccctcggc   600
ttaaccgagg aactgcatcg gaaactgttt ttcttgagtg cagaagagga gagtggaact   660
ccatgtgtag cggtggaatg cgtagatata tggaagaaca ccagtggcga aggcggctct   720
ctggtctgca actgacgctg aggctcgaaa gcatgggtag cgaacaggat tagataccct   780
ggtagtccat gccgtaaacg atgagtgcta agtgttggga ggtttccgcc tctcagtgct   840
gcagctaacg cattaagcac tccgcctggg gagtacgacc gcaaggttga actcaga      897
```

<210> SEQ ID NO 4
<211> LENGTH: 20
<212> TYPE: DNA
<213> ORGANISM: Artificial Sequence
<220> FEATURE:
<223> OTHER INFORMATION: 8F Primer

<400> SEQUENCE: 4

```
agagtttgat cctggctcag                                                 20
```

<210> SEQ ID NO 5
<211> LENGTH: 20
<212> TYPE: DNA
<213> ORGANISM: Artificial Sequence
<220> FEATURE:
<223> OTHER INFORMATION: 926R Primer

<400> SEQUENCE: 5

```
ccgtcaattc ctttragttt                                                 20
```